(12) United States Patent
Ranum et al.

(10) Patent No.: US 12,364,707 B2
(45) Date of Patent: *Jul. 22, 2025

(54) MANIPULATION OF eIF3 TO MODULATE REPEAT ASSOCIATED NON-ATG (RAN) TRANSLATION

(71) Applicant: University of Florida Research Foundation, Incorporated, Gainesville, FL (US)

(72) Inventors: Laura Ranum, Gainesville, FL (US); Fatma Ayhan, Lewisville, TX (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1172 days.

This patent is subject to a terminal disclaimer.

(21) Appl. No.: 17/159,288

(22) Filed: Jan. 27, 2021

(65) Prior Publication Data

US 2021/0236535 A1 Aug. 5, 2021

Related U.S. Application Data

(62) Division of application No. 16/091,444, filed as application No. PCT/US2017/026020 on Apr. 4, 2017, now Pat. No. 10,940,161.

(60) Provisional application No. 62/318,200, filed on Apr. 4, 2016.

(51) Int. Cl.
| | |
|---|---|
| A61K 31/7105 | (2006.01) |
| A61P 25/14 | (2006.01) |
| C07K 14/47 | (2006.01) |
| C07K 16/18 | (2006.01) |
| C12N 15/113 | (2010.01) |
| C12Q 1/68 | (2018.01) |

(52) U.S. Cl.
CPC .......... *A61K 31/7105* (2013.01); *A61P 25/14* (2018.01); *C07K 14/47* (2013.01); *C07K 14/4705* (2013.01); *C07K 16/18* (2013.01); *C12N 15/1138* (2013.01); *C07K 2317/34* (2013.01)

(58) Field of Classification Search
None
See application file for complete search history.

(56) References Cited

U.S. PATENT DOCUMENTS

| | | |
|---|---|---|
| 5,011,912 A | 4/1991 | Hopp et al. |
| 6,204,008 B1 | 3/2001 | Borneman et al. |
| 6,326,151 B1 | 12/2001 | Katze et al. |
| 6,342,581 B1 | 1/2002 | Rosen et al. |
| 7,008,796 B2 | 3/2006 | Wohlstadter et al. |
| 7,481,997 B1 | 1/2009 | Hardy |
| 8,993,663 B2 | 3/2015 | Megeney et al. |
| 9,448,232 B2 | 9/2016 | Petrucelli et al. |
| 10,295,547 B2 | 5/2019 | Ranum et al. |
| 10,509,045 B2 | 12/2019 | Ranum et al. |
| 10,663,475 B2 | 5/2020 | Ranum et al. |
| 10,940,161 B2 | 3/2021 | Ranum et al. |
| 11,034,974 B2 | 6/2021 | Ling et al. |
| 11,345,911 B2 | 5/2022 | Ranum et al. |
| 11,903,910 B2 | 2/2024 | Ranum et al. |
| 12,025,622 B2 | 7/2024 | Ranum et al. |
| 2002/0165355 A1 | 11/2002 | Meheus et al. |
| 2003/0233675 A1 | 12/2003 | Cao et al. |
| 2005/0042657 A1 | 2/2005 | Weese-Mayer et al. |
| 2006/0068434 A1 | 3/2006 | Stoerker |
| 2007/0004729 A1 | 1/2007 | Timmer et al. |
| 2007/0014810 A1 | 1/2007 | Baker et al. |
| 2007/0036760 A1 | 2/2007 | Wilson et al. |
| 2007/0093426 A1 | 4/2007 | Wormser |
| 2008/0188457 A1 | 8/2008 | Barlow et al. |
| 2008/0227699 A1 | 9/2008 | Chiba et al. |
| 2008/0248099 A1 | 10/2008 | Ishii |
| 2009/0074721 A1 | 3/2009 | Kim et al. |
| 2009/0143418 A1 | 6/2009 | Dixon et al. |
| 2009/0148866 A1 | 6/2009 | Datwyler et al. |
| 2009/0312395 A1 | 12/2009 | El-Tanani et al. |
| 2010/0298280 A1 | 11/2010 | Kioschis-Schneider et al. |
| 2012/0076785 A1 | 3/2012 | Nikolaev et al. |
| 2012/0094299 A1 | 4/2012 | Ranum et al. |
| 2012/0220534 A1 | 8/2012 | Levin et al. |
| 2013/0085169 A1 | 4/2013 | Baghdoyan et al. |
| 2013/0115603 A9 | 5/2013 | Ranum et al. |
| 2014/0100282 A1 | 4/2014 | Wong |
| 2014/0336133 A1 | 11/2014 | Miller et al. |

(Continued)

FOREIGN PATENT DOCUMENTS

| | | |
|---|---|---|
| CA | 3137666 A1 | 11/2020 |
| EP | 2 837 390 A1 | 2/2015 |

(Continued)

OTHER PUBLICATIONS

Extended European Search Report, mailed Nov. 26, 2021, in connection with Application No. EP 18860923.4.

(Continued)

*Primary Examiner* — Sean McGarry
(74) *Attorney, Agent, or Firm* — Wolf, Greenfield & Sacks, P.C.

(57) ABSTRACT

Methods and compositions for modulating repeat non-ATG protein (RAN protein) translation are provided. In some aspects, the disclosure relates to methods for treating a subject having a disease associated with RAN protein translation by administering the subject a modulator of eIF3 or an eIF3 subunit, or an antibody that bind to a RAN protein.

20 Claims, 18 Drawing Sheets

Specification includes a Sequence Listing.

(56) References Cited

U.S. PATENT DOCUMENTS

| | | |
|---|---|---|
| 2015/0361166 A1 | 12/2015 | Edbauer et al. |
| 2016/0025747 A1 | 1/2016 | Ranum et al. |
| 2016/0096800 A1 | 4/2016 | Walter et al. |
| 2016/0346297 A1 | 12/2016 | Sheehan |
| 2018/0050001 A1 | 2/2018 | During et al. |
| 2018/0292416 A1 | 10/2018 | Ranum et al. |
| 2019/0142858 A1 | 5/2019 | Ranum et al. |
| 2019/0153445 A1 | 5/2019 | Seow et al. |
| 2019/0285652 A1 | 9/2019 | Ranum et al. |
| 2020/0140846 A1 | 5/2020 | Ranum et al. |
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |
| 2020/0341012 A1 | 10/2020 | Ranum et al. |
| 2021/0285970 A1 | 9/2021 | Ranum et al. |
| 2022/0373559 A1 | 11/2022 | Ranum et al. |
| 2023/0002753 A1 | 1/2023 | Ranum et al. |
| 2023/0218730 A1 | 7/2023 | Ranum et al. |
| 2023/0288434 A1 | 9/2023 | Ranum et al. |
| 2024/0069039 A1 | 2/2024 | Ranum et al. |
| 2024/0269093 A1 | 8/2024 | Ranum et al. |
| 2024/0393348 A1 | 11/2024 | Ranum et al. |
| 2025/0041247 A1 | 2/2025 | Ranum et al. |

FOREIGN PATENT DOCUMENTS

| | | |
|---|---|---|
| EP | 2 948 471 A1 | 12/2015 |
| EP | 3440100 A1 | 2/2019 |
| JP | 2004-518437 A | 6/2004 |
| JP | 2004-520803 A | 7/2004 |
| JP | 2007-507223 A | 3/2007 |
| JP | 2012-501193 A | 1/2012 |
| JP | 2016-515208 A | 5/2016 |
| JP | 2016-180665 A | 10/2016 |
| JP | 2017-019773 A | 1/2017 |
| JP | 2017-205118 A | 11/2017 |
| JP | 2019-515894 A | 6/2019 |
| WO | WO 2001/75067 A2 | 10/2001 |
| WO | WO 2001/081581 A2 | 11/2001 |
| WO | WO 2002/040672 A2 | 5/2002 |
| WO | WO 2002/062945 A2 | 8/2002 |
| WO | WO 2005/033321 A2 | 4/2005 |
| WO | WO 2006/083800 A2 | 8/2006 |
| WO | WO 2009/144480 A1 | 12/2009 |
| WO | WO 2010/115033 A2 | 10/2010 |
| WO | WO 2010/132982 A1 | 11/2010 |
| WO | WO 2011/052906 A2 | 5/2011 |
| WO | WO 2013/030588 A1 | 3/2013 |
| WO | WO 2013/061163 A2 | 5/2013 |
| WO | WO 2013/172537 A1 | 11/2013 |
| WO | WO 2014/114303 A1 | 7/2014 |
| WO | WO 2014/114660 A1 | 7/2014 |
| WO | WO 2014/116865 A1 | 7/2014 |
| WO | WO 2014/159247 A1 | 10/2014 |
| WO | WO 2016/025692 A1 | 2/2016 |
| WO | WO 2017/055612 A1 | 4/2017 |
| WO | WO 2017/176813 A1 | 10/2017 |
| WO | WO 2018/035408 A1 | 2/2018 |
| WO | WO 2018/195110 A1 | 10/2018 |
| WO | WO 2019/060918 A1 | 3/2019 |
| WO | WO 2019/067587 A1 | 4/2019 |
| WO | WO 2021/007110 A1 | 1/2021 |
| WO | WO 2021/055880 A1 | 3/2021 |
| WO | WO 2021/231887 A1 | 11/2021 |

OTHER PUBLICATIONS

Extended European Search Report, mailed Jun. 11, 2021, in connection with Application No. EP 18859783.5.

Extended European Search Report, mailed Oct. 4, 2023, in connection with application No. EP 20865149.7.

Invitation to Pay Additional Fees, mailed Nov. 30, 2020, in connection with Application No. PCT/US2020/051671.

International Search Report and Written Opinion, mailed Feb. 9, 2021, in connection with Application No. PCT/US2020/051671.

International Preliminary Report on Patentability, mailed Mar. 31, 2022, in connection with Application No. PCT/US2020/051671.

Extended European Search Report, mailed Aug. 25, 2023, in connection with Application No. EP 20869039.6.

International Search Report and Written Opinion, mailed Dec. 31, 2020, in connection with Application No. PCT/US2020/051670.

International Preliminary Report on Patentability, mailed Apr. 7, 2022, in connection with Application No. PCT/US2020/051670.

Extended European Search Report, mailed Oct. 4, 2023, in connection with application No. EP 20874343.5.

Invitation to Pay Additional Fees, mailed Feb. 19, 2021, in connection with Application No. PCT/US2020/054976.

International Search Report and Written Opinion, mailed Apr. 23, 2021, in connection with Application No. PCT/US2020/054976.

International Preliminary Report on Patentability, mailed Apr. 21, 2022, in connection with Application No. PCT/US2020/054976.

Invitation to Pay Additional Fees, mailed Mar. 30, 2023, in connection with Application No. PCT/US2022/051530.

International Search Report and Written Opinion, mailed May 25, 2023, in connection with Application No. PCT/US2022/051530.

International Search Report and Written Opinion, mailed Jul. 19, 2023, in connection with Application No. PCT/US2023/063328.

[No Author Listed] Amersham ECL Western Blotting Detection Reagent. Retrieved from the internet under https://www.cytivalifesciences.com/en/us/shop/protein-analysis/blotting-and-detection/blotting-standards-and-reagents/amersham-ecl-western-blotting-detection-reagent-p-05748 on Feb. 22, 2022, 6 pages.

Bando et al., Double-strand RNA dependent protein kinase (PKR) is involved in the extrastriatal degeneration in Parkinson's disease and Huntington's disease. Neurochem Int. Jan. 2005;46(1):11-8. doi: 10.1016/j.neuint.2004.07.005.

Bañez-Coronel et al., Repeat-associated non-AUG (RAN) translation: insights from pathology. Lab Invest. Jul. 2019;99(7):929-942. doi: 10.1038/s41374-019-0241-x. Epub Mar. 27, 2019.

Bañez-Coronel et al., Sense and antisense RAN proteins in the CAG•CTG polyglutamine spinocerebellar ataxias. International Congress for Ataxia Research. Abstract ID 271. Nov. 1-4, 2022. 1 page.

Barzilai et al., Metformin as a Tool to Target Aging. Cell Metab. Jun. 14, 2016;23(6):1060-1065. doi: 10.1016/j.cmet.2016.05.011.

Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.

Benkirane et al., Oncogenic potential of TAR RNA binding protein TRBP and its regulatory interaction with RNA-dependent protein kinase PKR. EMBO J. Feb. 3, 1997;16(3):611-24. doi: 10.1093/emboj/16.3.611.

Brooks et al., Spinal and bulbar muscular atrophy: a trinucleotide-repeat expansion neurodegenerative disease. Trends Neurosci. Oct. 1995; 18(10):459-61. doi: 10.1016/0166-2236(95)94497-s.

Castelli et al., Mechanisms of repeat-associated non-AUG translation in neurological microsatellite expansion disorders. Biochem Soc Trans. Apr. 30, 2021;49(2):775-792. doi: 10.1042/BST20200690.

Chen et al., Antidiabetic drug metformin (GlucophageR) increases biogenesis of Alzheimer's amyloid peptides via up-regulating BACE1 transcription. Proc Natl Acad Sci U S A. Mar. 10, 2009;106(10):3907-12. doi: 10.1073/pnas.0807991106. Epub Feb. 23, 2009.

Cheng et al., C9ORF72 GGGGCC repeat-associated non-AUG translation is upregulated by stress through eIF2a phosphorylation. Nat Commun. Jan. 4, 2018;9(1):51. doi: 10.1038/s41467-017-02495-z.

Cleary et al., New developments in RAN translation: insights from multiple diseases. Curr Opin Genet Dev. Jun. 2017;44:125-134. doi: 10.1016/j.gde.2017.03.006. Epub Mar. 30, 2017. Author Manuscript, 18 pages.

Cleary et al., Repeat associated non-ATG (RAN) translation: new starts in microsatellite expansion disorders. Curr Opin Genet Dev. Jun. 2014;26:6-15. doi: 10.1016/j.gde.2014.03.002. Epub May 22, 2014. Author Manuscript, 20 pages.

(56) References Cited

OTHER PUBLICATIONS

Davidkin et al., Persistence of anti-mumps virus antibodies after a two-dose MMR vaccination. A nine-year follow-up. Vaccine. Nov. 1995;13(16):1617-22. doi: 10.1016/0264-410x(95)00064-8.
Foretz et al., Metformin: from mechanisms of action to therapies. Cell Metab. Dec. 2, 2014;20(6):953-66. doi: 10.1016/j.cmet.2014. 09.018. Epub Oct. 30, 2014.
Gantois et al., Metformin ameliorates core deficits in a mouse model of fragile X syndrome. Nat Med. Jun. 2017;23(6):674-677. doi: 10.1038/nm.4335. Epub May 15, 2017.
Gray et al., Comparability of serum prostate-specific antigen measurement between the Roche Diagnostics Elecsys 2010 and the Abbott Architect i2000. Ann Clin Biochem. May 2004;41(Pt 3):207-12. doi: 10.1258/000456304323019578.
Green et al., RAN translation at C9orf72-associated repeat expansions is selectively enhanced by the integrated stress response. Nat Commun. Dec. 8, 2017;8(1):2005. doi: 10.1038/s41467-017-02200-0.
Guerra et al., Human gene profiling in response to the active protein kinase, interferon-induced serine/threonine protein kinase (PKR), in infected cells. Involvement of the transcription factor ATF-3 IN PKR-induced apoptosis. J Biol Chem. Jul. 7, 2006;281(27):18734-45. doi: 10.1074/jbc.M511983200. Epub Apr. 13, 2006.
Jawaid et al., ALS disease onset may occur later in patients with pre-morbid diabetes mellitus. Eur J Neurol. May 2010;17(5):733-9. doi: 10.1111/j.1468-1331.2009.02923.x. Epub Jan. 13, 2010.
Kioumourtzoglou et al., Diabetes Mellitus, Obesity, and Diagnosis of Amyotrophic Lateral Sclerosis: A Population-Based Study. JAMA Neurol. Aug. 2015;72(8):905-11. doi: 10.1001/jamaneurol.2015. 0910. Author Manuscript, 15 pages.
Koide et al., Unstable expansion of CAG repeat in hereditary dentatorubral-pallidoluysian atrophy (DRPLA). Nat Genet. Jan. 1994;6(1):9-13. doi: 10.1038/ng0194-9.
Koob et al., An untranslated CTG expansion causes a novel form of spinocerebellar ataxia (SCA8). Nat Genet. Apr. 1999;21(4):379-84. doi: 10.1038/7710.
Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone. 0090803.
Liu et al., C9orf72 BAC Mouse Model with Motor Deficits and Neurodegenerative Features of ALS/FTD. Neuron. May 4, 2016;90(3):521-34. doi: 10.1016/j.neuron.2016.04.005. Epub Apr. 21, 2016.
Memmott et al., Metformin prevents tobacco carcinogen—induced lung tumorigenesis. Cancer Prev Res (Phila). Sep. 2010;3(9):1066-76. doi: 10.1158/1940-6207.CAPR-10-0055. Epub Sep. 1, 2010.
Mirkin, Expandable DNA repeats and human disease. Nature. Jun. 21, 2007;447(7147):932-40. doi: 10.1038/nature05977.
Moon et al., Neuronal Regulation of eIF2α Function in Health and Neurological Disorders. Trends Mol Med. Jun. 2018;24(6):575-589. doi: 10.1016/j.molmed.2018.04.001. Epub Apr. 30, 2018.
Nguyen et al., Repeat-Associated Non-ATG Translation: Molecular Mechanisms and Contribution to Neurological Disease. Annu Rev Neurosci. Jul. 8, 2019;42:227-247. doi: 10.1146/annurev-neuro-070918-050405. Epub Mar. 25, 2019. Author Manuscript, 24 pages.
Pakos-Zebrucka et al., The integrated stress response. EMBO Rep. Oct. 2016;17(10):1374-1395. doi: 10.15252/embr.201642195. Epub Sep. 14, 2016.
Park et al., TAR RNA-binding protein is an inhibitor of the interferon-induced protein kinase PKR. Proc Natl Acad Sci U S A. May 24, 1994;91(11):4713-7. doi: 10.1073/pnas.91.11.4713.
Peel et al., Double-stranded RNA-dependent protein kinase, PKR, binds preferentially to Huntington's disease (HD) transcripts and is activated in HD tissue. Hum Mol Genet. Jul. 15, 2001;10(15):1531-8. doi: 10.1093/hmg/10.15.1531.
Perez et al., CCG•CGG interruptions in high-penetrance SCA8 families increase RAN translation and protein toxicity. EMBO Mol Med. Nov. 8, 2021;13(11):e14095. doi: 10.15252/emmm. 202114095. Epub Oct. 11, 2021.

Sonenberg et al., Regulation of translation initiation in eukaryotes: mechanisms and biological targets. Cell. Feb. 20, 2009;136(4):731-45. doi: 10.1016/j.cell.2009.01.042.
Soragni et al., Repeat-Associated Non-ATG (RAN) Translation in Fuchs' Endothelial Corneal Dystrophy. Invest Ophthalmol Vis Sci. Apr. 1, 2018;59(5):1888-1896. doi: 10.1167/iovs.17-23265.
Taylor et al., Decoding ALS: from genes to mechanism. Nature. Nov. 10, 2016;539(7628):197-206. doi: 10.1038/nature20413. Author Manuscript, 28 pages.
Tian et al., Expanded CUG repeat RNAs form hairpins that activate the double-stranded RNA-dependent protein kinase PKR. RNA. Jan. 2000;6(1):79-87. doi: 10.1017/s1355838200991544.
Todd et al., CGG repeat-associated translation mediates neurodegeneration in fragile X tremor ataxia syndrome. Neuron. May 8, 2013;78(3):440-55. doi: 10.1016/j.neuron.2013.03.026. Epub Apr. 18, 2013. Erratum in: Neuron. Jul. 24, 2013;79(2):402.
Todd et al., Insights into the pathogenic mechanisms of Chromosome 9 open reading frame 72 (C9orf72) repeat expansions. J Neurochem. Aug. 2016;138 Suppl 1:145-62. doi: 10.1111/jnc. 13623. Epub Jun. 15, 2016.
Tsuji, S., Dentatorubral-pallidoluysian atrophy. Handb Clin Neurol. 2012;103:587-94. doi: 10.1016/B978-0-444-51892-7.00041-3.
Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.
Vishwakarma et al., Current molecular insight to reveal the dynamics of CAG repeating units in spinocerebellar ataxia. Intractable Rare Dis Res. May 2018;7(2):79-86. doi: 10.5582/irdr.2018.01039.
Wieben et al., Amplification-free long-read sequencing of TCF4 expanded trinucleotide repeats in Fuchs Endothelial Corneal Dystrophy. PLoS One. Jul. 5, 2019;14(7):e0219446. doi: 10.1371/journal. pone.0219446.
Zhou et al., Antibodies inhibit transmission and aggregation of C9orf72 poly-GA dipeptide repeat proteins. EMBO Mol Med. May 2017;9(5):687-702. doi: 10.15252/emmm.201607054.
Zhu et al., Suppression of PKR promotes network excitability and enhanced cognition by interferon-γ-mediated disinhibition. Cell. Dec. 9, 2011;147(6):1384-96. doi: 10.1016/j.cell.2011.11.029.
Zu et al., Metformin inhibits RAN translation through PKR pathway and mitigates disease in C9orf72 ALS/FTD mice. Proc Natl Acad Sci U S A. Aug. 4, 2020;117(31):18591-18599. doi: 10.1073/pnas. 2005748117. Epub Jul. 20, 2020. Supplementary Materials, 33 pages.
Zu et al., Non-ATG-initiated translation directed by microsatellite expansions. Proc Natl Acad Sci U S A. Jan. 4, 2011;108(1):260-5. doi: 10.1073/pnas.1013343108. Epub Dec. 20, 2010.
Zu et al., RAN Translation Regulated by Muscleblind Proteins in Myotonic Dystrophy Type 2. Neuron. Sep. 13, 2017;95(6):1292-1305.e5. doi: 10.1016/j.neuron.2017.08.039.
U.S. Appl. No. 16/851,690, filed Apr. 17, 2020, Ranum et al.
U.S. Appl. No. 16/695,717, filed Nov. 26, 2019, Ranum et al.
U.S. Appl. No. 16/605,992, filed Oct. 17, 2019, Ranum et al.
U.S. Appl. No. 16/650,721, filed Mar. 25, 2020, Ranum et al.
U.S. Appl. No. 16/650,016, filed Mar. 24, 2020, Ranum et al.
EP 14776090.4, Sep. 30, 2016, Extended European Search Report.
PCT/US2014/022670, Aug. 22, 2014, International Search Report and Written Opinion.
PCT/US2014/022670, Sep. 24, 2015, Internationai Preliminary Report on Patentability.
PCT/US2016/034738, Sep. 21, 2016, International Search Report and Written Opinion.
PCT/US2016/034738, Dec. 14, 2017, International Preliminary Report on Patentability.
EP 17779695.0, Oct. 18, 2019, Supplementary Partial European Search Report.
EP 17779695.0, Jan. 7, 2020, Extended European Search Report.
PCT/US2017/026020, Jul. 7, 2017, International Search Report and Written Opinion.
PCT/US2017/026020, Oct. 18, 2018, International Preliminary Report on Patentability.

(56) References Cited

OTHER PUBLICATIONS

EP 18786964.9, Dec. 17, 2020, Extended European Search Report.
PCT/US2018/028015, Jul. 27, 2018, International Search Report and Written Opinion.
PCT/US2018/028015, Oct. 31, 2019, International Preliminary Report on Patentability.
PCT/US2018/052913, Jan. 15, 2019, International Search Report and Written Opinion.
PCT/US2018/052913, Apr. 9, 2020, International Preliminary Report on Patentability.
PCT/US2018/052745, Dec. 6, 2018, International Search Report and Written Opinion.
PCT/US2018/052745, Apr. 9, 2020, International Preliminary Report on Patentability.
U.S. Appl. No. 17/322,604, filed May 17, 2021, Ranum et al.
U.S. Appl. No. 18/297,883, filed Apr. 10, 2023, Ranum et al.
U.S. Appl. No. 17/826,224, filed May 27, 2022, Ranum et al.
U.S. Appl. No. 18/403,100, filed Jan. 3, 2024, Ranum et al.
U.S. Appl. No. 17/761,764, filed Mar. 18, 2022, Ranum et al.
U.S. Appl. No. 17/762,543, filed Mar. 22, 2022, Ranum et al.
U.S. Appl. No. 17/767,549, filed Apr. 8, 2022, Ranum et al.
EP 18860923.4, Nov. 26, 2021, Extended European Search Report.
EP 188597835, Jun. 11, 2021, Extended European Search Report.
EP 20865149.7, Oct. 4, 2023, Extended European Search Report.
PCT/US2020/051671, Nov. 30, 2020, Invitation to Pay Additional Fees.
PCT/US2020/051671, Feb. 9, 2021, International Search Report and Written Opinion.
PCT/US2020/051671, Mar. 31, 2022, International Preliminary Report on Patentability.
EP 20869039.6, Aug. 25, 2023, Extended European Search Report.
PCT/US2020/051670, Dec. 31, 2020, International Search Report and Written Opinion.
PCT/US2020/051670, Apr. 7, 2022, International Preliminary Report on Patentability.
EP 20874343.5, Oct. 4, 2023, Extended European Search Report.
PCT/US2020/054976, Feb. 19, 2021, Invitation to Pay Additional Fees.
PCT/US2020/054976, Apr. 23, 2021, International Search Report and Written Opinion.
PCT/US2020/054976, Apr. 21, 2022, International Preliminary Report on Patentability.
PCT/US2022/051530, Mar. 30, 2023, Invitation to Pay Additional Fees.
PCT/US2022/051530, May 25, 2023, International Search Report and Written Opinion.
PCT/US2023/063328, Jul. 19, 2023, International Search Report and Written Opinion.
Extended European Search Report, mailed Sep. 30, 2016, in connection with Application No. EP14776090.4.
International Search Report and Written Opinion mailed on Aug. 22, 2014, in connection with Application No. PCT/US2014/022670.
International Preliminary Report on Patentability, mailed on Sep. 24, 2015, in connection with Application No. PCT/US2014/022670.
International Search Report and Written Opinion, mailed on Sep. 21, 2016, in connection with Application No. PCT/US2016/034738.
International Preliminary Report on Patentability, mailed on Dec. 14, 2017, in connection with Application No. PCT/US2016/034738.
Supplementary Partial European Search Report, mailed Oct. 18, 2019, in connection with Application No. EP 17779695.0.
Extended European Search Report, mailed Jan. 7, 2020, in connection with Application No. EP 17779695.0.
International Search Report and Written Opinion, mailed Jul. 7, 2017, in connection with Application No. PCT/US2017/026020.
International Preliminary Report on Patentability, mailed Oct. 18, 2018, in connection with Application No. PCT/US2017/026020.
Extended European Search Report, mailed Dec. 17, 2020, in connection with Application No. EP18786964.9.
International Search Report and Written Opinion, mailed Jul. 27, 2018, Application No. PCT/US2018/028015.
International Preliminary Report on Patentability, mailed Oct. 31, 2019, in connection with Application No. PCT/US2018/028015.
International Search Report and Written Opinion, mailed Jan. 15, 2019, in connection with Application No. PCT/US2018/052913.
International Preliminary Report on Patentability, mailed Apr. 9, 2020, in connection with for Application No. PCT/US2018/052913.
International Preliminary Report on Patentability, mailed Apr. 9, 2020, in connection with Application No. PCT/US2018/052745.
International Search Report and Written Opinion, mailed Dec. 6, 2019, in connection with Application No. PCT/US2018/052745.
[No Author Listed] EBNA1—Epstein-Barr nuclear antigen 1—Epstein-Barr virus (strain GD1) (HHV-4)—EBNA1 gene & protein, Jan. 2018. 2018. Retrieved from the internet under https://www.uniprot.org/uniprot/Q3KSS4 on Sep. 12, 2018. 6 pages.
[No Author Listed], Abstracts. Medgen. Mar. 4, 2016; 28(1):84-232. DOI: 10.1007/s11825-016-0083-5.
Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 Ran polySer protein preferentially accumulates in white matter regions and is regulated by eIF3F. EMBO J. Oct. 1, 2018;37(19). pii: e99023. doi: 10.15252/embj.201899023. Epub Sep. 11, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular α-synuclein prevents cell-to-cell aggregate transmission. J Neurosci. Sep. 26, 2012;32(39):13454-69.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Bañez-Coronel et al., RAN Translation in Huntington Disease. Neuron. Nov. 18, 2015;88(4):667-77. doi: 10.1016/j.neuron.2015.10.038. Author manuscript.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Functional genomics in *Drosophila* models of human disease. Briefings in Functional Genomics. Aug. 22, 2012;11(5):405-415.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.
Duan et al., Generation of polyclonal antiserum for the detection of methylarginine proteins. J Immunol Methods. Mar. 30, 2007;320(1-2):132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 6, 2009.
Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.
Jin et al., Metformin Protects Cells from Mutant Huntingtin Toxicity Through Activation of AMPK and Modulation of Mitochondrial

(56) References Cited

OTHER PUBLICATIONS

Dynamics. Neuromolecular Med. Dec. 2016; 18(4):581-592. doi: 10.1007/s12017-016-8412-z. Epub May 25, 2016.
Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.
Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.
Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.
Satoh et al., Dystrophic neurites express C9orf72 in Alzheimer's disease brains. Alzheimers Res Ther. Aug. 16, 2012;4(4):33. doi: 10.1186/alzrt136. 13 pages.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12):1563-9.
Trouth et al., Myasthenia gravis: a review. Autoimmune Dis. ;2012:874680. doi: 10.1155/2012/874680. Epub Oct. 31, 2012.
Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi: 10.1038/srep26120.
Welnowska et al., Translation of viral mRNA without active eIF2: the case of picornaviruses. PLoS One. 2011;6(7):e22230. doi: 10.1371/journal.pone.0022230. Epub Jul. 14, 2011.
Wojciechowska et al., RAN translation and frameshifting as translational challenges at simple repeats of human neurodegenerative disorders. Nucleic Acids Res. Oct. 29, 2014;42(19):11849-64. doi: 10.1093/nar/gku794. Epub Sep. 12, 2014.
Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.
Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.
Yu et al., Developing therapeutic antibodies for neurodegenerative disease. Neurotherapeutics. Jul. 2013;10(3):459-72. doi: 10.1007/s13311-013-0187-4.
Zhang et al., Aggregation-prone c9FTD/ALS poly(GA) RAN-translated proteins cause neurotoxicity by inducing ER stress. Acta Neuropathol. 2014;128:505-24.
Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.
International Preliminary Report on Patentability, mailed Jun. 13, 2024, in connection with Application No. PCT/US2022/051530.
International Preliminary Report on Patentability, mailed Sep. 12, 2024, in connection with Application No. PCT/US2023/063328.
[No Author Listed] CRC group Top> L. K. Housing> Query, after sampling and sampling, was conducted, kept still in whole blood ; CRC Corporation, Jun. 30, 2013. https://web.archive.org/web/20130630024235/http://www.crc-group.co.jp/crc/q_and_a/149.html.
Asokan et al., The AAV vector toolkit: poised at the clinical crossroads. Mol Ther. Apr. 2012;20(4):699-708. doi: 10.1038/mt.2011.287. Epub Jan. 24, 2012.
Cendelin et al., Consensus Paper: Strengths and Weaknesses of Animal Models of Spinocerebellar Ataxias and Their Clinical Implications. Cerebellum. Jun. 2022;21(3):452-481. doi: 10.1007/s12311-021-01311-1. Epub Aug. 10, 2021.
Tandon et al., Polyglutamine disorders: Pathogenesis and potential drug interventions. Life Sci. May 1, 2024;344:122562. doi: 10.1016/j.lfs.2024.122562. Epub Mar. 14, 2024.
William et al., Old friends on new paths: metformin as an early phase treatment in Huntington's Disease?, Medizinische Genetik, 28, pp. 215-216, Mar. 4, 2016 (Mar. 4, 2016) (Abstract).
U.S. Appl. No. 18/668,571, filed May 20, 2024, Ranum et al.
U.S. Appl. No. 18/715,436, filed May 31, 2024, Ranum et al.
U.S. Appl. No. 18/841,754, filed Aug. 27, 2024, Ranum et al.
PCT/US2022/051530, Jun. 13, 2024, International Preliminary Report on Patentability.
PCT/US2023/063328, Sep. 12, 2024, International Preliminary Report on Patentability.

FIG. 1A
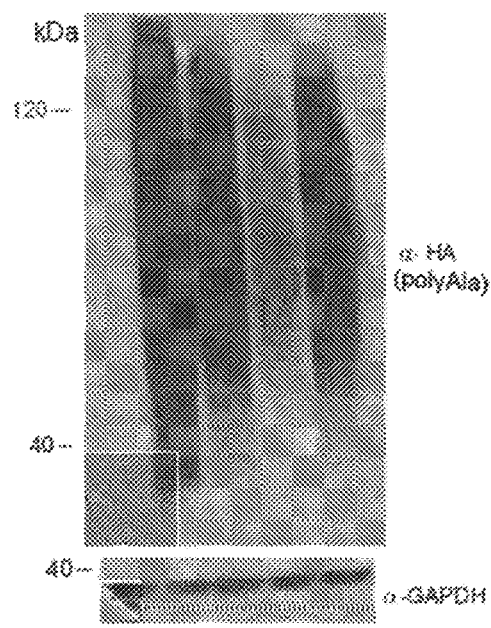
FIG. 1B
FIG. 1C (Ser)n SSSKARFSNMKDPG
SQGIGNRASANRVNLSVEA
GSQKRQSECKDK*

Flag-Ser-CT:

H2N-SSSSSSSSSS(dPEG4)CKK-amide polySer-Flag construct

SEQUENCE LISTING

```
<160> NUMBER OF SEQ ID NOS: 20

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1

Ala Ala Ala Ala Ala Ala Ala Ala Ala Ala Ala Ala Ala Ala Ala
1               5                   10                  15

Ala Ala Ala Ala
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Leu Leu Leu Leu Leu Leu Leu Leu Leu Leu Leu Leu Leu Leu Leu Leu
1               5                   10                  15

Leu Leu

<210> SEQ ID NO 3
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 3

Ser Ser Ser Ser Ser Ser Ser Ser Ser Ser Ser Ser Ser Ser Ser Ser
1               5                   10                  15

Ser Ser Ser Ser
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 4

Cys Cys Cys Cys Cys Cys Cys Cys Cys Cys Cys Cys Cys Cys Cys Cys
1               5                   10                  15

Cys Cys Cys Cys
            20

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 5

Gln Ala Gly Arg
1
```

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Leu Pro Ala Cys
1

<210> SEQ ID NO 7
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 7
agctgaagct tgttaaaaga agataatata tttaaaaaat gcag           44

<210> SEQ ID NO 8
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 8
agtctgaatt ccctagttct tggctccaga ctaac           35

<210> SEQ ID NO 9
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 9

Cys Ser Ser Ser Lys Ala Arg Phe Ser Asn Met Lys Asp
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Cys Arg Val Asn Leu Ser Val Glu Ala Gly Ser Gln Lys Arg Gln Ser
1               5                   10                  15

Glu

<210> SEQ ID NO 11
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 11

Val Lys Pro Gly Phe Leu Thr
1               5

<210> SEQ ID NO 12

-continued

```
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 12

Arg Val Asn Leu Ser Val Glu Ala Gly Ser Gln Lys Arg Gln Ser Glu
1               5                   10                  15

<210> SEQ ID NO 13
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 13
cagcagcagc agcag                                                    15

<210> SEQ ID NO 14
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 14

Ser Ser Ser Lys Ala Arg Phe Ser Asn Met Lys Asp Pro Gly Ser Gln
1               5                   10                  15

Gly Ile Gly Asn Arg Ala Ser Ala Asn Arg Val Asn Leu Ser Val Glu
            20                  25                  30

Ala Gly Ser Gln Lys Arg Gln Ser Glu Cys Lys Asp Lys
        35                  40                  45

<210> SEQ ID NO 15
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 15

Ser Ser Ser Lys Ala Arg Phe Ser Asn Met Lys Asp Pro Gly
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 16

Arg Val Asn Leu Ser Val Glu Ala Gly Ser Gln Lys Arg Gln Ser Glu
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by NH2
```

```
<220> FEATURE:
<221> NAME/KEY: MISC_FEATURE
<222> LOCATION: (10)..(11)
<223> OTHER INFORMATION: Modified by dPEG4
<220> FEATURE:
<221> NAME/KEY: MISC_FEATURE
<222> LOCATION: (13)..(13)
<223> OTHER INFORMATION: Modified by Amide

<400> SEQUENCE: 17

Ser Ser Ser Ser Ser Ser Ser Ser Ser Ser Cys Lys Lys
1               5                   10

<210> SEQ ID NO 18
<211> LENGTH: 309
<212> TYPE: DNA
<213> ORGANISM: Artificial Sequence
<220> FEATURE:
<223> OTHER INFORMATION: Synthetic Polynucleotide

<400> SEQUENCE: 18
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300
cagcagcag                                                             309

<210> SEQ ID NO 19
<211> LENGTH: 300
<212> TYPE: DNA
<213> ORGANISM: Artificial Sequence
<220> FEATURE:
<223> OTHER INFORMATION: Synthetic Polynucleotide

<400> SEQUENCE: 19
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300

<210> SEQ ID NO 20
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 20

Ser Ser Ser Ser Ser Ser Ser Ser Ser Ser Ser Ser Ser Ser Ser Ser
1               5                   10                  15

Ser Ser Ser Ser Ser Ser Ser Ser Ser Ser Ser Ser Ser Ser
            20                  25                  30

Ser Ser Ser Ser Ser Ser Ser Ser Ser Ser Ser Ser Ser Ser Ser
        35                  40                  45
```

```
Ser Ser Ser Ser Ser Ser Ser Ser Ser Ser Ser Ser Ser Ser Ser
        50                  55                  60
Ser Ser Ser Ser Ser Ser Ser Ser Ser Ser Ser Ser Ser Ser Ser
65                  70                  75                  80
Ser Ser
```

MANIPULATION OF eIF3 TO MODULATE REPEAT ASSOCIATED NON-ATG (RAN) TRANSLATION

RELATED APPLICATIONS

This application is a division of Ser. No. 16/091,444, filed Oct. 4, 2018, which is a national stage filing under 35 U.S.C. § 371 of international application number PCT/US2017/026020, filed Apr. 4, 2017, and claims the benefit under 35 U.S.C. 119(e) of U.S. provisional Application Ser. No. 62/318,200, filed on Apr. 4, 2016, entitled "MANIPULATION OF EIF3 TO MODULATE REPEAT ASSOCIATED NON-ATG (RAN) TRANSLATION", the entire contents of each of which are incorporated herein by reference.

FEDERALLY SPONSORED RESEARCH

This invention was made with government support under grant number R37 NS040389 awarded by the National Institutes of Health. The government has certain rights in the invention.

BACKGROUND

Since the initial discovery of repeat associated non-ATG (RAN) translation, a growing number of disease-associated repeats have been found to undergo RAN translation. Although RAN protein toxicity has been shown in transfected cells and model systems, suggesting the relevance of RAN translation to disease pathogenesis, the understanding of the mechanism of RAN translation has not improved since the initial discovery of RAN translation. It has been observed that hairpin-forming CAG but not non-hairpin forming CAA expansions undergo RAN translation in transfected cells. Additionally, it has been observed that all of the other repeat expansions reported to undergo RAN translation are also capable of forming complex RNA structures such as intrastrand hairpins and G-quadraplexes. These data suggest RAN translation occurs in an RNA structure-dependent manner. Additionally, larger repeat expansions are typically associated with higher levels of RAN protein accumulation in transfected cells, suggesting an increased number of repeats favor RAN translation. Additional cis- and trans-factors involved in RAN translation remain to be elucidated.

SUMMARY OF INVENTION

In some embodiments, aspects of the disclosure provide a method of modulating repeat associated non-ATG protein (RAN protein) translation by contacting a cell expressing a repeat associated non-ATG protein (RAN protein) with an effective amount of a eukaryotic initiation factor 3 (eIF3) modulating agent.

In some embodiments, the RAN protein is a poly-Alanine, poly-Leucine, poly-Serine, poly-Cysteine, poly-Leu-Pro-Ala-Cys (SEQ ID NO: 6) (e.g., associated with DM2), poly-Gln-Ala-Gly-Arg (SEQ ID NO: 5) (e.g., associated with DM2), poly-Gly-Pro, poly-Gly-Arg, poly-Gly-Ala (e.g., sense C9orf72 ALS/FTD), or poly-Pro-Ala, poly-Pro-Arg, poly-Gly-Pro (e.g., antisense C9orf72 ALS/FTD). In some embodiments, the RAN protein is not poly-Glutamine. In some embodiments, the RAN protein comprises between about 10 and about 100 poly-amino acid repeats. In some embodiments, the RAN protein comprises between about 20 and about 75 poly-amino acid repeats. In some embodiments, the RAN protein comprises between about 30 and about 200 poly-amino acid repeats. In some embodiments, the RAN protein comprises at least 35 poly-amino acid repeats. In some embodiments, the RAN protein comprises at least 100 poly-amino acid repeats. In some embodiments, the RAN protein comprises at least 200 poly-amino acid repeats (e.g., at least 500, 1000, 2000, 2500, 5000, 10000, etc. poly-amino acid repeats).

In some embodiments, the RAN protein is encoded by a gene associated with Huntington's disease (HD, HDL2), Fragile X Syndrome (FRAXA). Spinal Bulbar Muscular Atrophy (SBMA), Dentatorubropallidoluysian Atrophy (DRPLA), Spinocerebellar Ataxia 1 (SCA1). Spinocerebellar Ataxia 2 (SCA2). Spinocerebellar Ataxia 3 (SCA3), Spinocerebellar Ataxia 6 (SCA6), Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuch's Corneal Dystrophy (e.g., CTG181).

In some embodiments, the eIF3 modulating agent is a protein, such as an antibody, nucleic acid, or small molecule. In some embodiments, the eIF3 modulating agent is an inhibitory nucleic acid. In some embodiments, the inhibitory nucleic acid is an interfering RNA selected from the group consisting of dsRNA, siRNA, shRNA, mi-RNA, and artificial miRNA (ami-RNA). In some embodiments, the inhibitory nucleic acid is an antisense nucleic acid, such as an antisense oligonucleotide (ASO), or a nucleic acid aptamer, such as an RNA aptamer). In some embodiments, the interfering RNA is a siRNA. In some embodiments, the interfering RNA binds specifically (e.g., hybridizes) to a nucleic acid encoding eIF3 (e.g., a nucleic acid encoding an eIF3 subunit).

It should be appreciated that an eIF3 modulating agent can reduce the expression of a nucleic acid encoding an eIF3 subunit (e.g., an eIF3F nucleic acid) or expression of an eIF3 protein (e.g., an eIF3f subunit). In some embodiments, the eIF3 modulating agent reduces expression of an eIF3 subunit selected from the group consisting of eIF3a, eIF3b, eIF3c, eIF3d, eIF3e, eIF3f, eIF3g, eIF3h, eIF3i, eIF3j, eIF3k, eIF3l, and eIF3m. In some embodiments, the eIF3 inhibitor reduces expression of eIF3f or eIF3m. In some embodiments, the eIF3 modulating agent reduces expression of an eIF3 subunit-encoding nucleic acid selected from the group consisting of eIF3A, eIF3B, eIF3C, eIF3D, eIF3E, eIF3F, eIF3G, eIF3H, eIF3I, eIF3J, eIF3K, eIF3L, and eIF3M. In some embodiments, the eIF3 inhibitor reduces expression of eIF3f or eIF3m. In some embodiments, the eIF3 inhibitor reduces expression of eIF3F or eIF3M.

In some embodiments, the eIF3 modulating agent increases expression of an eIF3 subunit selected from the group consisting of eIF3a, eIF3h, eIF3c, eIF3d, eIF3e, eIF3f, eIF3g, eIF3h, eIF3i, eIF3j, eIF3k, eIF3l, and eIF3m. In some embodiments, the eIF3 inhibitor increases expression of eIF3h. In some embodiments, the eIF3 modulating agent increases expression of an eIF3 subunit-encoding nucleic acid selected from the group consisting of eIF3A, eIF3B, eIF3C, eIF3D, eIF3E, eIF3F, eIF3G, eIF3H, eIF3I, eIF3J, eIF3K, eIF3L, and eIF3M. In some embodiments, the eIF3 inhibitor increases expression of eIF3f or eIF3m. In some embodiments, the eIF3 inhibitor increases expression of eIF3F or eIF3M.

In some embodiments, the cell is located in a subject. In some embodiments, the cell is located in the brain of the subject, optionally in the white matter of the brain. In some embodiments, the subject is an animal. In some embodiments, the subject is a mammal. In some embodiments, the subject is a human.

In some embodiments, aspects of the disclosure provide a method of treating a disease associated with repeat associated non-ATG protein (RAN protein) translation by administering to a subject expressing a repeat associated non-ATG protein (RAN protein) an effective amount of a eukaryotic initiation factor 3 (eIF3) modulating agent.

In some embodiments, the RAN protein is not poly-Glutamine. In some embodiments, the RAN protein is a poly-Alanine, poly-Leucine, poly-Serine, poly-Cysteine, poly-Glutamine, poly-Leu-Pro-Ala-Cys (SEQ ID NO: 6) (e.g., associated with DM2), poly-Gln-Ala-Gly-Arg (SEQ ID NO: 5) (e.g., associated with DM2), poly-Gly-Pro, poly-Gly-Arg, poly-Gly-Ala (e.g., sense C9orf72 ALS/FTD), or poly-Pro-Ala, poly-Pro-Arg, poly-Gly-Pro (e.g., antisense C9orf72 ALS/FTD). In some embodiments, the RAN protein comprises at least 35 poly-amino acid repeats. In some embodiments, the RAN protein comprises between about 10 and about 100 poly-amino acid repeats. In some embodiments, the RAN protein comprises between about 20 and about 75 poly-amino acid repeats. In some embodiments, the RAN protein comprises between about 30 and about 200 poly-amino acid repeats. In some embodiments, the RAN protein comprises at least 100 poly-amino acid repeats. In some embodiments, the RAN protein comprises at least 200 poly-amino acid repeats (e.g., at least 500, 1000, 2000, 2500, 5000, 10000, etc. poly-amino acid repeats).

In some embodiments, the disease associated with repeat non-ATG protein (RAN protein) translation is Huntington's disease (HD, HDL2), Fragile X Syndrome (FRAXA), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2). Spinocerebellar Ataxia 3 (SCA3), Spinocerebellar Ataxia 6 (SCA6), Spinocerebellar Ataxia 7 (SCA7), Spinocerebellar Ataxia 8 (SCA8). Spinocerebellar Ataxia 12 (SCA12), or Spinocerebellar Ataxia 17 (SCA17), amyotrophic lateral sclerosis (ALS). Spinocerebellar ataxia type 36 (SCA36), Spinocerebellar ataxia type 29 (SCA29). Spinocerebellar ataxia type 10 (SCA10), myotonic dystrophy type 1 (DM1), myotonic dystrophy type 2 (DM2), or Fuch's Corneal Dystrophy (e.g., CTG181).

In some embodiments, the eIF3 modulating agent is a protein, such as an antibody, nucleic acid, or small molecule. In some embodiments, the eIF3 modulating agent is an inhibitory nucleic acid. In some embodiments, the inhibitory nucleic acid is an interfering RNA selected from the group consisting of dsRNA, siRNA, shRNA, mi-RNA, and ami-RNA. In some embodiments, the inhibitory nucleic acid is an antisense nucleic acid, such as an antisense oligonucleotide (ASO), or a nucleic acid aptamer, such as an RNA aptamer. In some embodiments, the interfering RNA is a siRNA.

In some embodiments, the eIF3 modulating agent reduces expression of eIF3f. In some embodiments, the eIF3 modulating agent reduces expression of eIF3m. In some embodiments, the eIF3 modulating agent reduces expression of eIF3F. In some embodiments, the eIF3 modulating agent reduces expression of eIF3M. In some embodiments, both an eIF3 modulating agent that reduces expression of eIF3f and an eIF3 modulating agent that reduces expression of eIF3m are administered to the subject.

In some embodiments, the method further comprises administering an additional therapeutic agent for the disease associated with repeat non-ATG protein (RAN protein) translation. In some embodiments, the additional therapeutic agent is an antibody (e.g., an antibody that binds specifically to a RAN repeat expansion or an antibody that binds specifically to a unique region of a RAN protein that is C-terminal to the repeat expansion) or a further inhibitory nucleic acid. In some embodiments, the antibody binds specifically to a poly-Ser RAN repeat expansion. In some embodiments, the antibody binds to a C-terminal region of a protein comprising a poly-Ser RAN repeat expansion.

In some embodiments, the eIF3 modulating agent increases expression of eIF3h.

In some embodiments, the subject is an animal. In some embodiments, the subject is a mammal. In some embodiments, the subject is a human.

In some embodiments, a composition comprises one or more (e.g., 2, 3, 4, 5, or more) agents that modulate expression and/or activity of eIF3 (e.g., of one or more subunits of eIF3).

In some aspects, the disclosure provides a method for treating a disease associated with repeat non-ATG protein (RAN protein) translation, the method comprising administering to a subject expressing a repeat non-ATG protein (RAN protein) an effective amount of an antibody that binds specifically to a RAN repeat expansion, or an antibody that binds specifically to a unique region of a RAN protein that is C-terminal to the repeat expansion.

In some embodiments, the antibody binds to a poly-serine (poly-Ser) repeat expansion. In some embodiments, the antibody binds to the unique region of the RAN protein that is C-terminal to the repeat expansion. In some embodiments the unique region of the RAN protein that is C-terminal to the repeat expansion is comprises a sequence set forth in SEQ ID NO: 9.

In some embodiments, an antibody as described by the disclosure (e.g., an antibody that binds specifically to a RAN repeat expansion, or an antibody that binds specifically to a unique region of a RAN protein that is C-terminal to the repeat expansion) targets (e.g., immunospecifically binds to) a RAN protein aggregate in a subject. In some embodiments, an anti-RAN protein antibody binds to an intracellular RAN protein (e.g., binds to a RAN protein in the cytoplasm or nucleus of a cell). In some embodiments, an anti-RAN protein antibody binds to an extracellular RAN protein (e.g., binds to a RAN protein outside of the extracellular membrane of a cell).

These and other aspects of the application are described in more detail herein and illustrated by the following non-limiting drawings.

BRIEF DESCRIPTION OF DRAWINGS

FIGS. 1A-1C show eIF3F knockdown leads to a decrease in polyAla RAN. FIG. 1A shows a schematic showing the plasmid used. ATG at the polyGln frame. The sequence corresponds to SEQ ID NO: 18. FIGS. 1B-1C show Western blots showing decrease in polyAla but not polyGln in the presence of eIF3F knockdown (KD).

FIG. 2A shows a schematic of eIF3 complex organization. FIG. 2B shows a RAN expression construct. ATG is present in polyAla frame. The sequence corresponds to SEQ ID NO: 18. FIGS. 2C-2D show polyAla levels are reduced with eIF3M siRNA treatment but increased by eIF3H siRNA treatment.

FIG. 3A shows a RAN expression construct carrying no close-cognate start sites. The sequence corresponds to SEQ ID NO: 19. FIG. 3B shows a Western blot demonstrating a RAN decrease three frames, polySer show both soluble (upper) and insoluble (lower) fractions. FIG. 3C shows a Western blot showing efficient knockdown of eIF3F protein.

FIG. 4A shows ATXN8 gene and the proteins expressed across CAG repeat. Amino acid and nucleic acid sequences (top to bottom) are represented by SEQ ID NOs: 11-13. FIG. 4B shows the expression of the polySer frame in ATXN8 is eIF3F-knockdown sensitive because of the AUG and near cognate in polyGln and polyAla frames.

FIG. 5A shows a C9orf72 minigene (top) and protein blot showing eIF3F siRNA reduces GP RAN protein (bottom). FIG. 5B shows a DM2 minigene (top) and protein blot showing eIF3F siRNA reduces QAGR RAN protein (bottom).

FIG. 6A shows the amino acid sequence of polySer RAN protein with a unique C-terminus (SEQ ID NO: 14). Peptide sequences used to generate rabbit polyclonal antibodies are underlined (SSSKARFSNMKDPG, SEQ ID NO: 15) and RVNLS-VEAGSQKRQSE, SEQ ID NO: 16). FIG. 6B shows a schematic diagram of the Flag-Ser-CT construct expressing an ATG-initiated N-terminal Flag epitope tagged polySer expansion protein followed by the endogenous C-terminal sequence. The sequence corresponds to SEQ ID NO: 20. Colocalization of immunofluorescence (IF) staining using α-Flag and α-SerCT1 in HEK293T cells transfected with Flag-Ser-CT but not preimmune serum. FIG. 6C shows colocalization of immunofluorescence (IF) staining using α-Flag and α-SerCT2 in HEK293T cells transfected with Flag-Ser-CT but not pcDNA3.1. FIG. 6D shows immunoblots showing detection of recombinant polySer protein using α-Flag (left) and α-SerCT2 (right) in the lysates of HEK293Tcells transfected with Flag-Ser-CT (second lanes) but not pcDNA3.1 (first lanes). FIG. 6E shows immunohistochemistry (IHC) of SCA8 BAC mouse cerebellum indicating that polyGln but not polySer accumulates in Purkinje cells. In contrast, polySer is found in the molecular layer and cerebellar white matter. (Inset: higher magnification of molecular layer and white matter.

FIG. 8A shows vacuolization shown by H&E, associated demyelination shown by luxol fast blue staining (LFB), and axonal degeneration shown by α-SMI-32 observed in sites of polySer accumulation shown by SerCT in deep cerebellar white matter was shown in the cerebellum and brainstem SCA8 BAC mice but not in NT mice. FIG. 8B shows demyelination shown by LFB, and axonal degeneration shown by α-SMI-32, observed at sites with polySer accumulation as detected by the SerCT antibody in SCA8 human autopsy tissue. FIG. 8C shows immunohistochemistry (IHC) using CC1 (α-APC) antibody shows significantly lower numbers of mature oligodendrocytes in SCA8 BAC mice compared to NT mice (NT n=5, SCA8 BAC n=5; ** p<0.0001; Mean±SEM; unpaired t test). FIG. 8D shows immunofluorescence using α-GFAP antibody shows significant increase in astrogliosis in SCA8 BAC mice compared to NT mice (NT n=3, SCA8 BAC n=3,  p<0.01; Mean±SEM; unpaired t test).

FIG. 9A shows a bar graph showing relative Eif3f expression levels in SCA8 BAC mice compared to littermates. p<0.0001; Mean±SEM; unpaired t test). FIG. 9B shows a schematic diagram showing constructs used for eIF3F knockdown experiments. All constructs have a tag in each of the three reading frame. M indicates methionine initiated reading frames. The sequences all correspond to SEQ ID NO: 18. FIG. 9C shows dot blot detection of polySer expression using α-FLAG antibody showing decrease in RAN poly-Ser but not ATG polySer when cells are co-transfected with eIF3F siRNA. FIG. 9D shows quantification of polySer detection. * p<0.05; n.s. no significance; Mean±SEM; unpaired t test. FIG. 9E shows detection of polyAla expression using α-HA antibody showing decrease in RAN poly-Ala but not ATG polyAla when cells are co-transfected with eIF3F siRNA. FIG. 9F shows quantification of polyAla detection. * p<0.05; n.s. no significance; Mean±SEM; unpaired t test.

FIG. 10A shows protein blotting of RAN protein expression detected with α-FLAG antibody showing decrease in RAN protein accumulation in cells co-transfected with GGGGCC or CAGG construct with eIF3F siRNA and increase in RAN protein accumulation in cells co-transfected with CCTG and eIF3F siRNA. FIG. 10B shows quantification of protein blots * p<0.05; n.s. no significance; Mean±SEM; unpaired t test. FIG. 10C shows eIF3F knockdown decreased levels of GP and QAGR RAN proteins expressed from constructs lacking an ATG initiation codon and increased levels of LPAC tetrapeptide protein expressed across CCUG expansion RNAs.

FIG. 11A shows a schematic diagram of putative proteins translated from sense and antisense transcripts arising from the CAG repeat. FIG. 11B shows the peptide sequence (SEQ ID NO: 17) used to generate the anti-Ser antibody (top) and a poly-Ser expression construct having a C-terminal FLAG tag (bottom). FIG. 11C shows poly-Ser detected in cells by immunoblot using the anti-Ser antibody. FIG. 11D shows immunofluorescence detection of poly-Ser having a C-terminal FLAG-tag by anti-FLAG and anti-Ser antibodies. FIG. 11E shows immunohistochemistry (IHC) staining of human SCA8 and control autopsy tissue using anti-Ser antibody.

DETAILED DESCRIPTION OF INVENTION

Figure 2A:
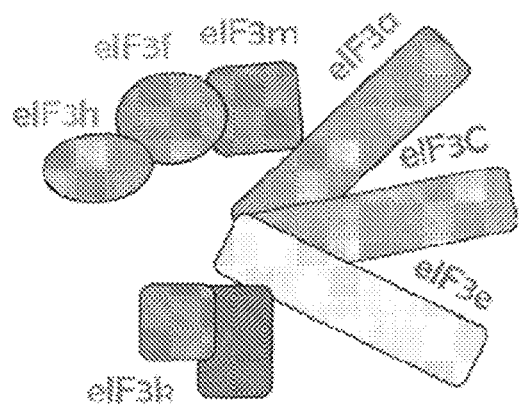
FIGS. 2A-2D show eIF3F and eIF3M but not eIF3H knockdown decrease RAN in polyAla frame.
Figure 2B:
Figure 2C:
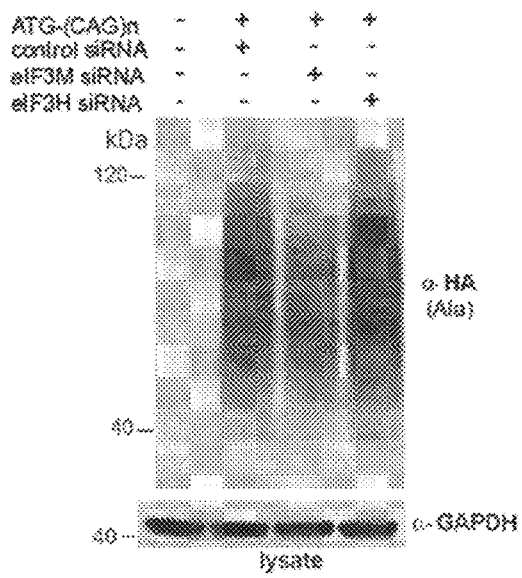
Figure 2D:
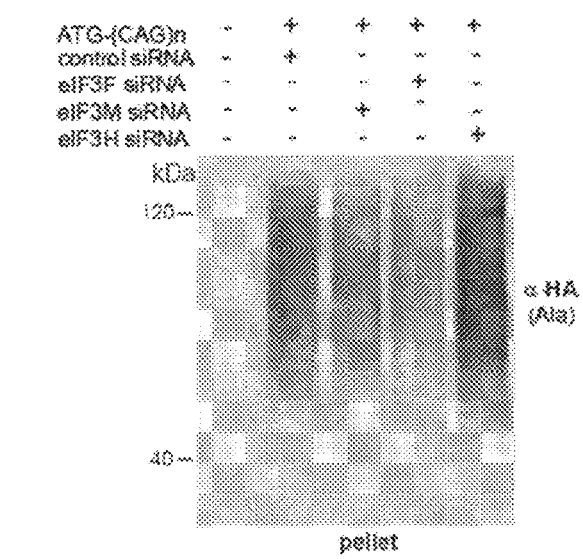

In eukaryotes, the protein translation machinery including ribosomes, initiation factors (eIFs) and specific steps of translation initiation and elongation are well conserved. However, it has been reported that components of the translation machinery including ribosomal proteins, ribosomal RNAs, tRNAs and eIF3 subunits vary between cell types and developmental stages. According to aspects of this disclosure, cell or tissue specific heterogeneity of one or more of these factors (e.g., one or more eIF3 subunits) accounts, in some embodiments, for the variability of RAN protein accumulation in brain.

Eukaryotic initiation factor 3 (eIF3) is a multiprotein complex that is involved with the initiation phase of eukaryotic protein translation. Generally, in humans eIF3 comprises 13 non-identical subunits (e.g., eIF3a-m). Mammalian eIF3, the largest most complex initiation factor, comprises up to 13 non-identical subunits. Typically, eIF3f is involved in many steps of translation initiation including stabilization of the ternary complex, mediating binding of mRNA to 40S subunit and facilitating dissociation of 40S and 60S ribosomal subunits. In some embodiments, the other non-conserved mammalian eIF3 subunits can play a modulatory role in eIF3 function and it effect on RAN translation (e.g., eIF3m). In some embodiments, eIF3 complex has been observed to interact with viral and cellular IRES in an RNA structure dependent manner, indicating it is role in non-canonical translation events. In some embodiments, eIF3f plays an important role in RAN translation and manipulation of eIF3F/eIF3f or other eIF3 subunits (e.g., eIF3M/eIF3m) can be useful to modulate RAN protein expression.

RAN Protein Translation

Aspects of the disclosure relate to the discovery that one or more eIF3 subunits are regulators of repeat-associated non-ATG (RAN) protein translation. A "RAN protein (repeat-associated non-ATG translated protein)" is a polypeptide translated from bidirectionally transcribed sense or antisense RNA sequences carrying a nucleotide expansion in the absence of an AUG initiation codon. Generally. RAN proteins comprise expansion repeats of an amino acid, termed poly amino acid repeats. For example, "AAAAAAAAAAAAAAAAAAAA" (poly-Alanine) (SEQ ID NO: 1), "LLLLLLLLLLLLLLLLLLLL" (poly-Leucine) (SEQ ID NO: 2). "SSSSSSSSSSSSSSSSSSSS" (poly-Serine) (SEQ ID NO: 3), or "CCCCCCCCCCCCCCCCCCCC" (poly-Cysteine) (SEQ ID NO: 4) are poly amino acid repeats that are each 20 amino acid residues in length. RAN proteins can have a poly amino acid repeat of at least 25, at least 30, at least 40, at least 50, at least 60, at least 70, at least 80, at least 90, at least 100, or at least 200 amino acid residues in length. In some embodiments, a RAN protein has a poly amino acid repeat more than 200 amino acid residues in length.

Generally, RAN proteins are translated from abnormal repeat expansions (e.g., CAG repeats) of DNA. Without wishing to be bound by any particular theory, RAN protein accumulation (e.g., in the nucleus or cytoplasm of a cell) disrupts cellular function and induces cellular toxicity. Thus, in some embodiments, translation and accumulation of RAN proteins is associated with a disease or disorder, for example a neurodegenerative disease or disorder. Examples of disorders and diseases associated with RAN protein translation and accumulation include but are not limited to spinocerebellar ataxia type 8 (SCA8), myotonic dystrophy type 1 (DM1), fragile X tremor ataxia syndrome (FXTAS), and C9ORF72 amyotrophic lateral sclerosis/frontotemporal dementia (ALS/FTD).

Methods of Treating Diseases and Disorders Associated with RAN Protein Translation or Accumulation In some embodiments, compositions and methods described by the disclosure are useful for reducing or inhibiting RAN protein translation or accumulation in a cell or a subject (e.g., a subject having a disorder or disease associated with RAN translation). In some embodiments, a cell is in vitro. In some embodiments, a subject is a mammalian subject. In some embodiments, a subject is a human subject.

In some aspects, the disclosure provides a method of treating a disease associated with repeat non-ATG protein (RAN protein) translation by administering to a subject expressing a repeat non-ATG protein (RAN protein) an effective amount of a eukaryotic initiation factor 3 (eIF3) modulating agent.

In some aspects, the disclosure provides a method of treating a disease associated with repeat non-ATG protein (RAN protein) translation by administering to a subject expressing a repeat non-ATG protein (RAN protein) an antibody (e.g., an antibody that binds specifically to a RAN repeat expansion or an antibody that binds specifically to a unique region of a RAN protein that is C-terminal to the repeat expansion). In some embodiments, the antibody binds specifically to a poly-Ser RAN repeat expansion. In some embodiments, the antibody hinds to a C-terminal region of a protein comprising a poly-Ser RAN repeat expansion.

In some embodiments, the disease associated with repeat non-ATG protein (RAN protein) translation is Huntington's disease (HD, HDL2). Fragile X Syndrome (FRAXA), Spinal Bulbar Muscular Atrophy (SBMA), Dentatorubropallidoluysian Atrophy (DRPLA). Spinocerebellar Ataxia 1 (SCA1), Spinocerebellar Ataxia 2 (SCA2), Spinocerebellar Ataxia 3 (SCA3), Spinocerebellar Ataxia 6 (SCA6). Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS). Spinocerebellar ataxia type 36 (SCA36). Spinocerebellar ataxia type 29 (SCA29). Spinocerebellar ataxia type 10 SCA10), myotonic dystrophy type 1 (DM1), myotonic dystrophy type 2 (DM2), or Fuch's Corneal Dystrophy (e.g., CTG181).

As used herein, an "effective amount" is a dosage of a therapeutic agent sufficient to provide a medically desirable result, such as treatment or amelioration of one or more signs or symptoms caused by a disease or disorder associated with RAN protein translation or accumulation (e.g., a neurodegenerative disease). The effective amount will vary with the age and physical condition of the subject being treated, the severity of the disease or disorder (e.g., the amount of RAN protein accumulation, or cellular toxicity caused by such an accumulation) in the subject, the duration of the treatment, the nature of any concurrent therapy, the specific route of administration and the like factors within the knowledge and expertise of the health practitioner.

In some embodiments, methods for treating a disease associated with repeat non-ATG protein (RAN protein) translation described by the disclosure further comprise administering to the subject one or more additional therapeutic agents. The identification and selection of appropriate additional therapeutic agents is within the capabilities of a person of ordinary skill in the art, and will depend upon the disease from which the subject is suffering. For example, in some embodiments one or more therapeutic agents for Huntington's disease (e.g. tetrabenazine, amantadine, chlorpromazine, etc.). Fragile X Syndrome (e.g., selective serotonin reuptake inhibitors, carbamazepine, methylphenidate, Trazodone, etc.), Spinocerebellar Ataxia (e.g., baclofen, riluzole, amantadine, varenicline, etc.), or amyotrophic lateral sclerosis (ALS) (e.g., riluzole, etc.), myotonic dystrophy type 1 (tideglusib, mexiletine, etc.) are administered to the subject.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDT, and nebulizers.

In some embodiments, a treatment for a disease associated with RAN protein expression is administered to the central nervous system (CNS) of a subject in need thereof. As used herein, the "central nervous system (CNS)" refers to all cells and tissues of the brain and spinal cord of a subject, including but not limited to neuronal cells, glial cells, astrocytes, cerebrospinal fluid, etc. Modalities of administering a therapeutic agent to the CNS of a subject include direct injection into the brain (e.g., intracerebral injection, intraventricular injection, intraparenchymal injection, etc.), direct injection into the spinal cord of a subject (e.g., intrathecal injection, lumbar injection, etc.), or any combination thereof.

In some embodiments, a treatment as described by the disclosure is systemically administered to a subject, for example by intravenous injection. Systemically administered therapeutic molecules (e.g., eIF3 modulating agents or anti-RAN protein antibodies) can be modified, in some embodiments, in order to improve delivery of the molecules to the CNS of a subject. Examples of modifications that improve CNS delivery of therapeutic molecules include but are not limited to co-administration or conjugation to blood brain barrier-targeting agents (e.g., transferrin, melanotransferrin, low-density lipoprotein (LDL), angiopeps, RVG peptide, etc., as disclosed by Georgieva et al. *Pharmaceuticals* 6(4): 557-583 (2014)), coadministration with BBB disrupting agents (e.g., bradykinins), and physical disruption of the BBB prior to administration (e.g., by MRI-Guided Focused Ultrasound), etc.

An eIF3 modulating agent, or an anti-RAN protein antibody (e.g., an antibody that binds to a RAN protein) may be delivered by any suitable modality known in the art. In some embodiments, an eIF3 modulating agent (e.g., an eIF3 interfering RNA, or an antibody that hinds to a RAN protein) is delivered to a subject by a vector, such as a viral vector (e.g., adenovirus vector, recombinant adeno-associated virus vector (rAAV vector), lentiviral vector, etc.) or a plasmid-based vector.

Aspects of the disclosure relate to the surprising discovery that robust SCA8 polySer RAN accumulation was detected within the deep cerebellar white matter in SCA8 mice and SCA8 human autopsy tissue. Thus, in some embodiments of methods described by the disclosure, the effective amount of eIF3 modulator is delivered to the white matter of the subject's brain.

eIF3 Modulators

In some embodiments, one or more subunits of eIF3 regulate RAN translation. In some embodiments, one or more agents that modulate expression (e.g., increase expression, or decrease expression) of an eIF3 subunit (e.g., eIF3f, eIF3m, eIF3h, or other eIF3 subunit) can be used to modulate RAN translation in a cell or in a subject (e.g., a subject having a disease or condition associated with RAN translation). In some aspects, the disclosure is based on the discovery that, in some embodiments, an isoform of the F subunit of the eIF3 complex (eIF3f) regulates RAN translation in certain areas of the brain, for example in the white matter regions of human brain.

In aspects, the disclosure relates to the discovery that administration of one or more modulators of eIF3 (e.g., one or more activators, or one or more inhibitors) to a subject (e.g., a cell of a subject) can be used to regulate translation of repeat-associated non-ATG (RAN) translation in one or more proteins. As used herein, a "modulator of eIF3" refers to an agent that directly or indirectly affects the expression level or activity of an eIF3 protein complex, or an eIF3 complex subunit (e.g., eIF3f, eIF3m, etc.). A modulator can be an activator of eIF3 or an eIF3 subunit (e.g., increase the expression or activity of eIF3 or an eIF3 subunit) or an inhibitor of eIF3 or an eIF3 subunit (e.g., decrease the expression or activity of eIF3 or an eIF3 subunit).

Generally, a direct modulator functions by interacting with (e.g., interacting with or binding to) a gene encoding eIF3 (or an eIF3 subunit), or an eIF3 protein complex, or an eIF3 subunit. Generally, an indirect modulator functions by interacting with a gene or protein that regulates the expression or activity of eIF3 or an eIF3 subunit (e.g., does not directly interact with a gene or protein encoding eIF3 or an eIF3 subunit). In some embodiments, a modulator of eIF3 is a selective modulator. A "selective modulator" refers to a modulator of eIF3 that preferentially modulates activity or expression of one type of eIF3 subunit compared with other types of eIF3 subunits. In some embodiments, a modulator of eIF3 is a selective modulator of eIF3f.

An eIF3 inhibitor can be a protein (e.g., antibody), nucleic acid, or small molecule. Examples of proteins that inhibit eIF3 (e.g., an eIF3 subunit) include but are not limited to polyclonal anti-eIF3 antibodies, monoclonal anti-eIF3 antibodies. Measles Virus N protein, Viral stress-inducible protein p56, etc. Examples of nucleic acid molecules that inhibit eIF3 (e.g., an eIF3 subunit) include but are not limited to dsRNA, siRNA, miRNA, etc. that target a gene encoding an eIF3 subunit. Examples of small molecule inhibitors of eIF3 include but are not limited to mTOR inhibitors (e.g., rapamycin, PP242), S6 kinase (S6K) inhibitors, etc.

In some embodiments, the eIF3 modulating agent is an inhibitory nucleic acid. In some embodiments, the inhibitory nucleic acid is an interfering RNA selected from the group consisting of dsRNA, siRNA, shRNA, mi-RNA, and ami-RNA. In some embodiments, the inhibitory nucleic acid is an antisense nucleic acid (e.g., an antisense oligonucleotide (ASO)) or a nucleic acid aptamer (e.g., an RNA aptamer). Generally, an inhibitory RNA molecule can be unmodified or modified. In some embodiments, an inhibitory RNA molecule comprises one or more modified oligonucleotides, e.g., phosphorothioate-, 2'-O-methyl-, etc.-modified oligonucleotides, as such modifications have been recognized in the art as improving the stability of oligonuclotides in vivo.

In some embodiments, the interfering RNA comprises a sequence that is complementary with between 5 and 50 continuous nucleotides (e.g., 5, 6, 7, 8, 9, 10, 11, 12, 13, 14, 15, 16, 17, 18, 19, 20, 21, 22, 23, 24, 25, about 30, about 35, about 40, or about 50 continuous nucleotides) of a nucleic acid sequence (such as an RNA sequence) encoding an eIF3 subunit. Examples of nucleic acid sequences encoding eIF3 subunits include GenBank Accession No. NM_003750.2 (eIF3a), GenBank Accession No. NM_003751.3 (eIF3b), GenBank Accession No. NM_003752.4 (eIF3c), GenBank Accession No. NM_003753.3 (eIF3d), GenBank Accession No. NM_001568.2 (eIF3e), GenBank Accession No. NM_003754.2 (eIF3f), GenBank Accession No. NM_003755.4 (eIF3g), GenBank Accession No.

NM_003756.2 (eIF3h), GenBank Accession No. NM_003757.3 (eIF3i). GenBank Accession No. NM_003758.3 (eIF3j), GenBank Accession No. NM_013234.3 (eIF3k). GenBank Accession No. NM_016091.3 (eIF3l), GenBank Accession No. NM_006360.5 (eIF3m), etc. In some embodiments, the interfering RNA is a siRNA. In some embodiments, an eIF3f siRNA is administered (e.g., Dharmacon Cat #J-019535-08). In some embodiments, an eIF3m siRNA is administered (e.g., Dharmacon Cat #J-016219-12). In some embodiments, an eIF3h siRNA is administered (e.g., Dharmacon Cal #J-003883-07).

In some embodiments, eIF3f is a negative regulator of RAN translation and decreased levels of human eIF3f are associated with decreased accumulation of RAN protein in cells. In some embodiments. RAN translation (e.g., in cells expressing a RAN protein) is sensitive to eIF3f knockdown unlike translation from close cognate or AUG translation. In some embodiments, the translational machinery used for RAN translation is distinct from AUG and near AUG translation machinery in a cell.

In some embodiments, increasing eIF3f levels or activity (e.g., via ectopic expression of eIF3f) can increase RAN translation. In some embodiments, this can be useful to increase RAN translation efficiency or induce RAN translation in cells (e.g., to create cellular or animal models of RAN translation). In some embodiments, eIF3f can be added to an in vitro cell-free translation system to support or promote RAN translation.

In some embodiments, one or more modulators (e.g., one or more activators, or one or more inhibitors) of one or more subunits of eIF3 are administered to a subject to treat a disease associated with an expansion of a nucleic acid repeat (e.g., associated with a repeat-associated non-ATG translation). For example, in some embodiments, a subject is administered 2, 3, 4, 5, 6, 7, 8, 9, or 10 modulators of one or more subunits of eIF3.

In certain microsatellite expansion disorders such as C9-ALS/FTD, RAN proteins from the GGGGCC repeat expansion are shown to accumulate in gray matter regions. Two of the three antisense reading frames carry an in-frame AUG start codon. According to aspects of the disclosure, the in-frame AUG and near AUG codon can account for the broader RAN protein accumulation in this disease (e.g., C9-ALS/FTD) beyond white matter regions. In some embodiments. RAN translation occurs in the presence of an upstream AUG initiation codon, and modulation of eIF3f/F affects protein accumulation in those reading frames (e.g. PR and GP made from antisense GGCCCC expansion transcripts in C9orf72 ALS/FTD).

In some embodiments, eIF3f regulates RAN translation for reading frames without any near-cognate start codons. In some embodiments, RAN translation for reading frames without any near-cognate start codons contributes to white matter specific accumulation of RAN proteins from these frames. Accordingly, in some embodiments the accumulation of RAN proteins in the white matter of a subject can be modulated by modulating eIF3 as described herein. In some embodiments, eIF3f modulation may modulate RAN protein accumulation in other non-white matter tissues.

In some embodiments, eIF3f in white matter regions may induce peptides from the repeat containing transcripts (more than 60% of human genome consists of repetitive elements) under non-pathological conditions. Interestingly, the human MBP gene which encodes for one of the most abundant white matter specific proteins, myelin basic protein, contains a highly polymorphic yet non-pathogenic (TGGA)n repeat within the first exon (Boylan et al., 1990). In some embodiments, MPB and/or other white-matter-specific genes that contain repeat expansions may be translated via RAN translation and give rise to peptides in human white matter. According to aspects of the disclosure, translation of such peptides can be regulated via eIF3 as described herein.

Anti-RAN Protein Antibodies

In some aspects, the disclosure relates to antibodies that bind specifically to a RAN repeat expansion or antibodies that bind specifically to a unique region of a RAN protein that is C-terminal to the repeat expansion. In some embodiments, the antibody binds specifically to a poly-Ser RAN repeat expansion. In some embodiments, the antibody binds to a C-terminal region of a protein comprising a poly-Ser RAN repeat expansion. In some embodiments, an anti-RAN antibody binds to an intracellular RAN protein. In some embodiments, an anti-RAN antibody binds to an extracellular RAN protein.

An anti-RAN antibody can be a polyclonal antibody or a monoclonal antibody. Typically, polyclonal antibodies are produced by inoculation of a suitable mammal, such as a mouse, rabbit or goat. Larger mammals are often preferred as the amount of serum that can be collected is greater. Typically, an antigen (e.g., an antigen comprising a poly-Ser repeat region) is injected into the mammal. This induces the B-lymphocytes to produce IgG immunoglobulins specific for the antigen. This polyclonal IgG is purified from the mammal's serum. Monoclonal antibodies are generally produced by a single cell line (e.g., a hybridoma cell line). In some embodiments, an anti-RAN antibody is purified (e.g., isolated from serum).

Numerous methods may be used for obtaining anti-RAN antibodies. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen (e.g., a RAN protein) may be used as the immunogen, e.g., recombinant antigen, naturally occurring forms, any variants or fragments thereof. One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597 WO92/18619; WO 91/17271; WO 92/20791: WO 92/15679; WO 93/01288; WO 92/01047: WO 92/09690; and WO 90/02809.

In addition to the use of display libraries, the specified antigen (e.g., one or more RAN proteins, such as poly-Ser) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., made chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494. United Kingdom Patent GB 2177096B.

Antibodies can also be humanized by methods known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals are within the scope of the invention (see, e.g., Green et al. (1994) Nature Genetics 7, 13; and U.S. Pat. Nos. 5,545,806 and 5,569,825).

For additional antibody production techniques, see Antibodies: A Laboratory Manual, Second Edition. Edited by Edward A. Greenfield. Dana-Farber Cancer Institute, ©2014. The present disclosure is not necessarily limited to any particular source, method of production, or other special characteristics of an antibody.

These and other aspects of the application are illustrated by the following non-limiting examples.

EXAMPLES

Example 1

More than 40 diseases are caused by microsatellite expansion mutations. The mechanisms by which repeat expansions mutations make proteins is variable. Expansion mutations can encode aggregate prone expansion proteins when they are expressed as part of an ATG-initiated open reading frame. Expansions can result in proteins in the presence of a close-cognate AUG-like initiation codon (typically one that varies from AUG by one nucleotide). In these cases the canonical protein translation machinery is typically used. Additionally, hairpin forming expansion mutations can also express expansion proteins in all three reading frames without an AUG initiation codon. This process is called repeat associated non-ATG (RAN) translation has been reported in a growing number of neurological diseases including spinocerebellar ataxia type 8, myotonic dystrophy, amyotrophic lateral sclerosis and frontotemporal dementia.

This example describes that modulation of the eIF3 complex (e.g., via an inhibitory agent, such as RNAi molecule(s)) affects RAN translation. This example describes siRNA knockdown of the eIF3F and eIF3M RNAs encoding the eIF3f and eIF3m protein subunits of the eIF3 complex reduce steady state levels of RAN proteins expressed across CAG, CAGG, CCUG and G4C2 expansion mutations. Conversely, overexpression of eIF3f and eIF3m, in some embodiments, increases RAN translation. This discovery has potential therapeutic implications for a broad category of diseases that are caused by microsatellite expansion mutations.

Decreased Levels of eIF3F Results in Downregulation of RAN Translation in the Absence of an AUG or Close Cognate AUG-Like Initiation Codon.

To investigate the role of eIF3F in RAN translation siRNA was used to knock-down eIF3F expression in HEK293T cells. A co-transfection experiment was performed using a repeat containing plasmid. ATG-(CAG)exp and control siRNA, eIF3F siRNA, or as a negative control. MRI1 siRNA (an eIF2B subunit-like protein). The plasmid ATG-(CAG)n contains an ATG start codon in the polyGln frame. Since the polySer expansion protein expressed from this construct has solubility issues, polyAla was used as a read-out for RAN translation. A dramatic decrease in polyAla expression in the cells transfected with ATG-(CAG)n plasmid along with eIF3F specific siRNA compared to both the control and MRI1 specific siRNA transfections was observed. In contrast. ATG-initiated polyGln expression does not appear to be affected by eIF3F knock-down, indicating canonical translation is not as sensitive as RAN translation to eIF3F levels (FIGS. 1A-1C).

The effects of two other eIF3 subunits, eIF3m and eIF3h, which directly interact with eIF3F, were investigated. It has been shown that eIF3-m, -a, -c, -e, -l, -k subunits are assembled through interaction of their polymerization domains. The -f and -h subunits bind to each other and are attached to the rest of the complex through the interactions between -f and -m. Downregulation of eIF3m show similar decreases in the levels of polyAla RAN protein. This is consistent with the decreases seen with eIF3f decreases because eIF3f is loaded on the rest of the complex through eIF3m.

The second binding partner, eIF3h, shows the opposite effect with knockdown of eIF3H siRNA increasing levels of polyAla RAN protein indicating that the eIF3h subunit normally prevents RAN translation (FIGS. 2A-D). The eIF3h subunit is reported to mediate translation from upstream open reading frames (uORFs) at AUG or close cognate initiation codons, indicating that this factor favors initiation at AUG or near-cognate codon AUG-like codons and may negatively regulate RAN translation. Thus, variants of the eIF3 complex will, in some embodiments, affect the efficiency of canonical and RAN translation. Specifically, when eIF3h is absent from the core complex, eIF3f can still bind to the core eIF3 complex and favor RAN translation and downregulate canonical translation.

Figure 3A:
FIGS. 3A-3C show eIF3F regulates RAN translation in all three frames across CAG expansions.
Figure 3B:
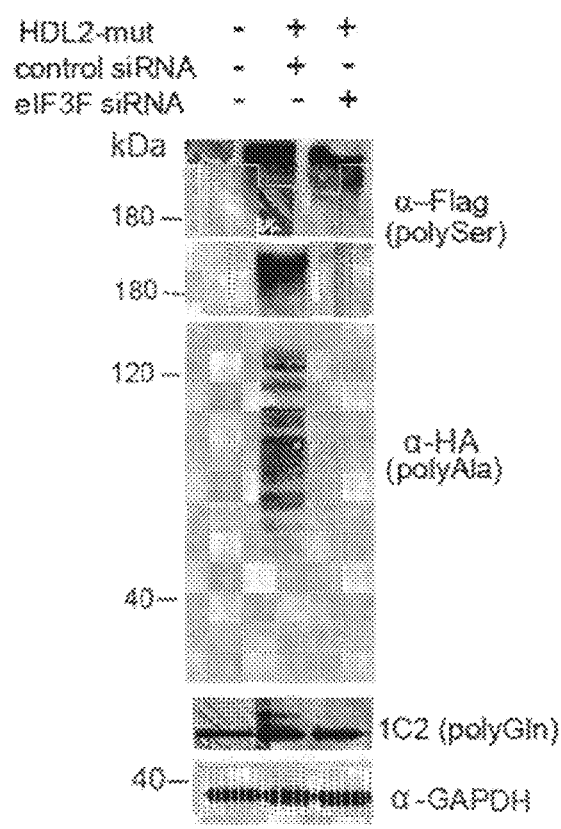
Figure 3C:
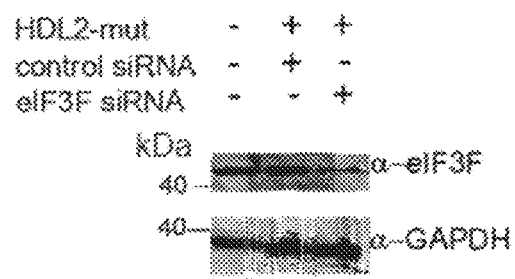

In order to investigate if the modulatory effects of eIF3f is polyAla-specific, a second plasmid containing expanded CAG repeats with a modified HDL2 5' flanking sequence upstream of the repeat (HDL2-mut) was examined. This construct does not contain any AUG or near AUG start codons between the stop codons and repeat tract in any of the reading frames, eIF3f downregulation leads to decreased RAN protein accumulation in all three frames (FIGS. 3A-3B). Since polySer RAN protein does not run well in the polyacrylamide gel, it is shown in both insoluble and soluble fraction. Efficient knock-down of the protein levels of eIF3f is also shown (FIG. 3C).

Figure 4A:
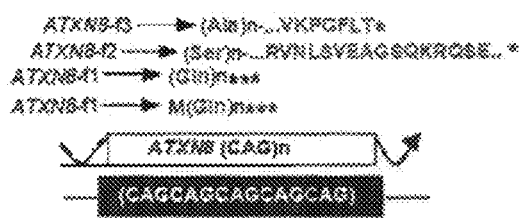
FIGS. 4A-4B show the effect of eIF3F knockdown in the context of ATXN8.
Figure 4B:
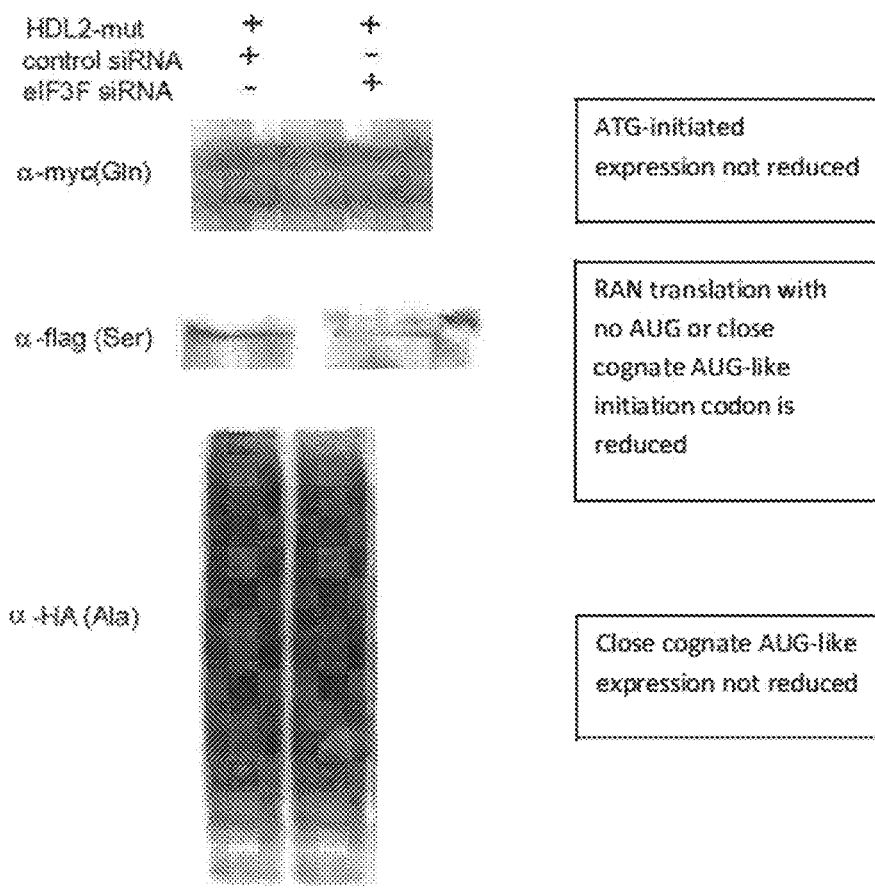

The effects of eIF3f knockdown on RAN translation within the ATXN8 context were examined (FIGS. 4A-4B). A construct with 5' flanking region from ATXN8 locus (KMQ-3T) was used. There is an ATG start codon in frame with polyGln. Double transfection experiments with this KMQ-3T plasmid and eIF3f targeting siRNA revealed that protein translation only from the polySer frame is sensitive to eIF3f levels, but polyGln and polyAla remained unaffected by the knockdown of eIF3f. This result on polyGln translation indicates that an in-frame AUG start codon drives the expression of polyGln via canonical translation. Additionally, there is a near cognate AUA codon in frame with polyAla. AUA codons is shown to be used at ~60% efficiency to start canonical translation in rabbit reticulolysates and could be driving canonical translation in polyAla frame in this context as well. Thus, modulatory effects of eIF3f is only present for polySer frame that does not contain any of the reported near-cognate start sites.

Figure 5A:
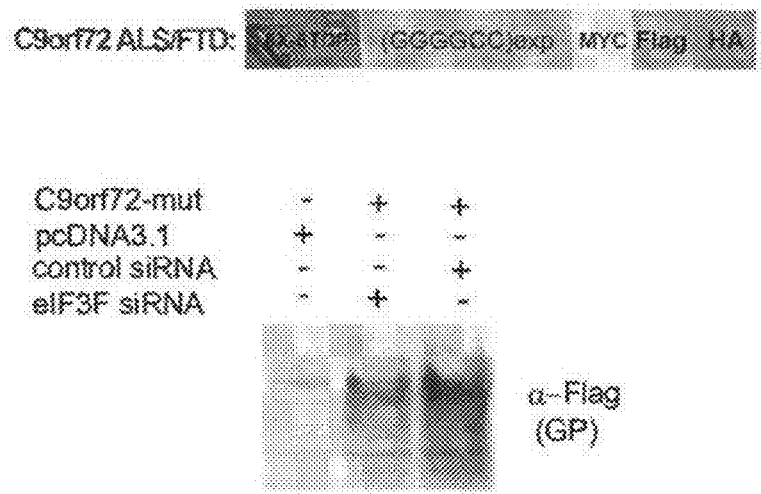
FIGS. 5A-5B show the effect of eIF3F in C9orf72 (ALS) and DM2 contexts.
Figure 5B:
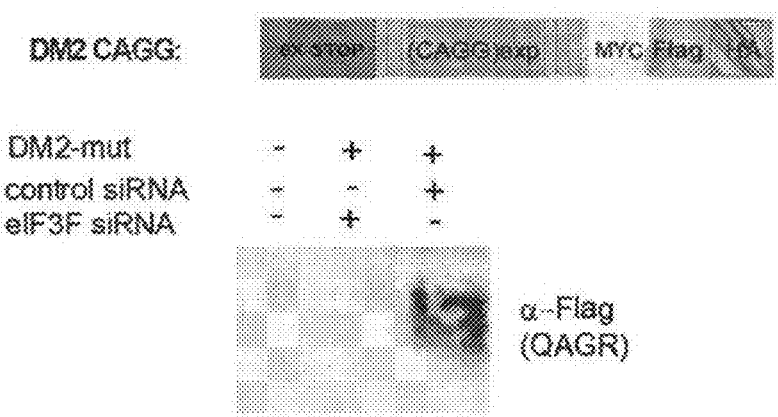

The effects of eIF3f knockdown on RAN translation within the ALS and DM2 contexts were examined. FIGS. 5A-5B show the effect of eIF3F in C9orf72 (ALS) and DM2 contexts. FIG. 5A shows a C9orf72 minigene (top) and protein blot showing eIF3F siRNA reduces GP RAN protein (bottom). FIG. 5B shows a DM2 minigene (top) and protein blot showing eIF3F siRNA reduces QAGR RAN protein (bottom).

Taken together, these experiments in transfected cells indicate that RAN translation, which initiates without close-cognate codon usage and met-tRNA involvement uses a specific translation machinery that involves the eIF3f and eIF3m subunits.

Example 2

PolySer Proteins Accumulate in White Matter Regions of the Brain

Figures 6A, 6B:
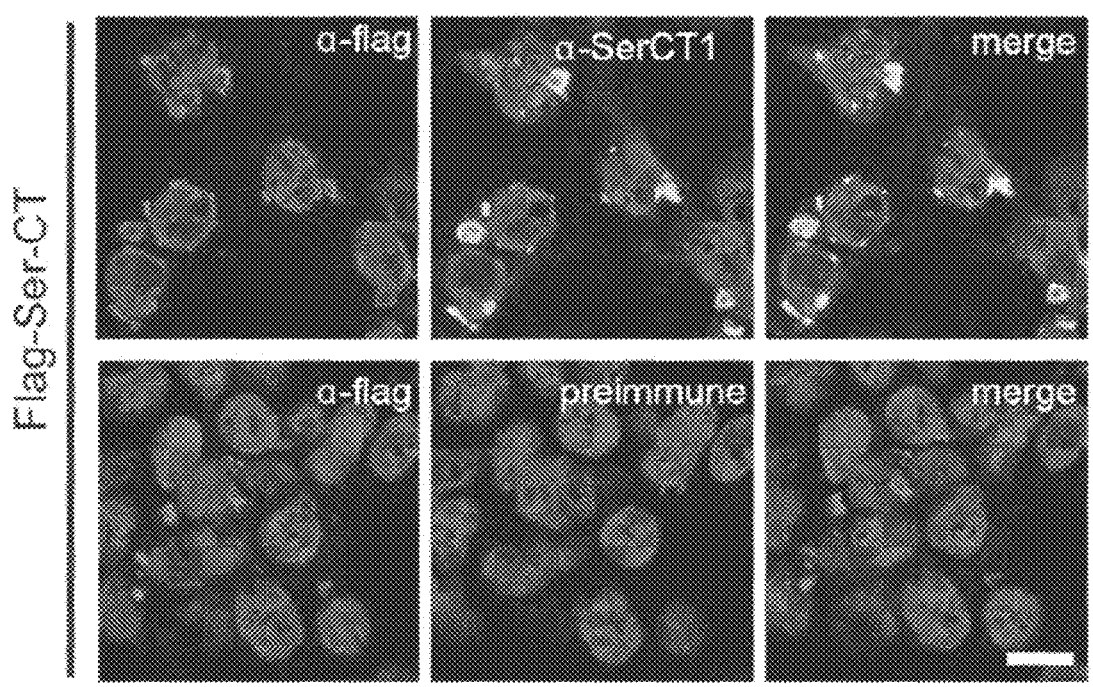
FIGS. 6A-6E show PolySer proteins accumulate in white matter regions of the brain.
Figure 6C:
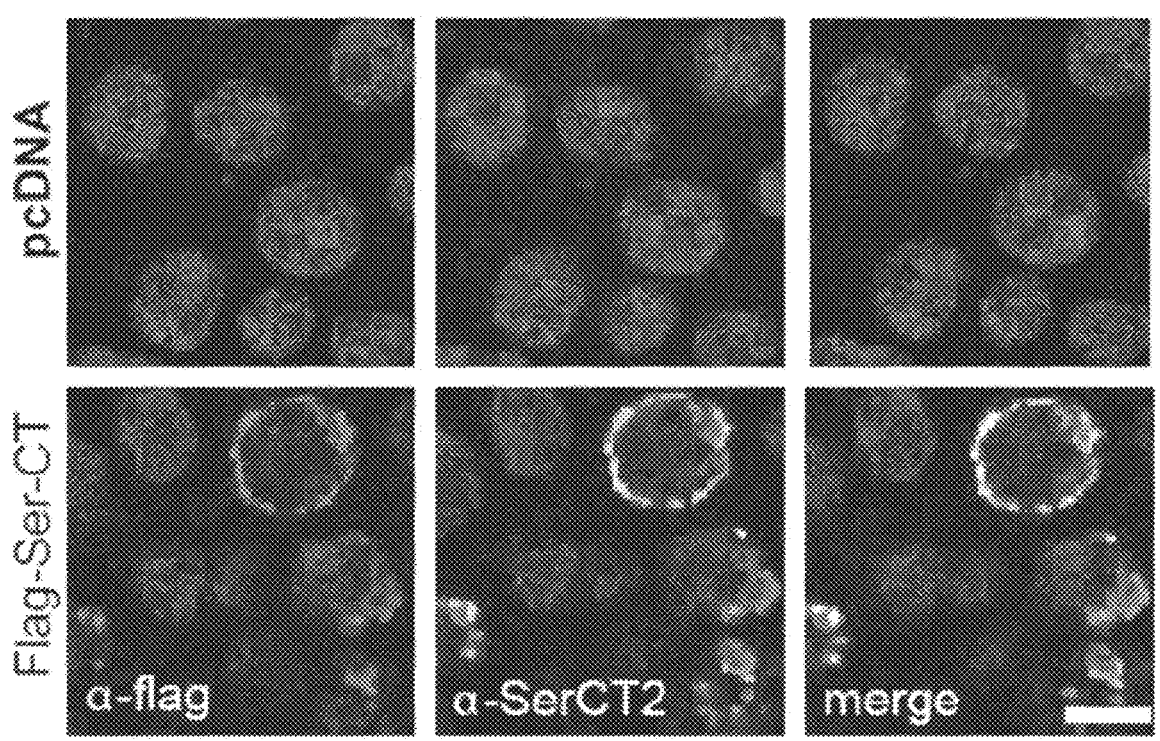
Figure 6D:
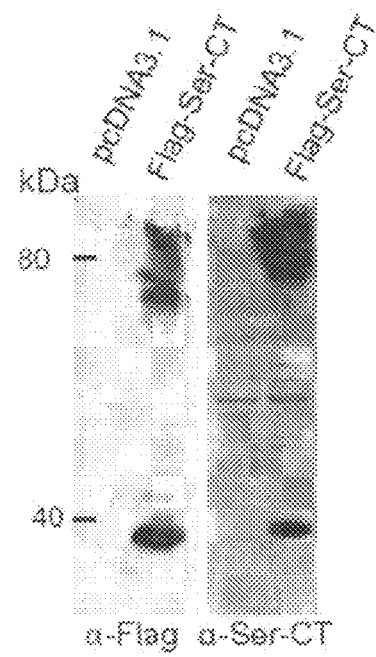
Figure 6E:
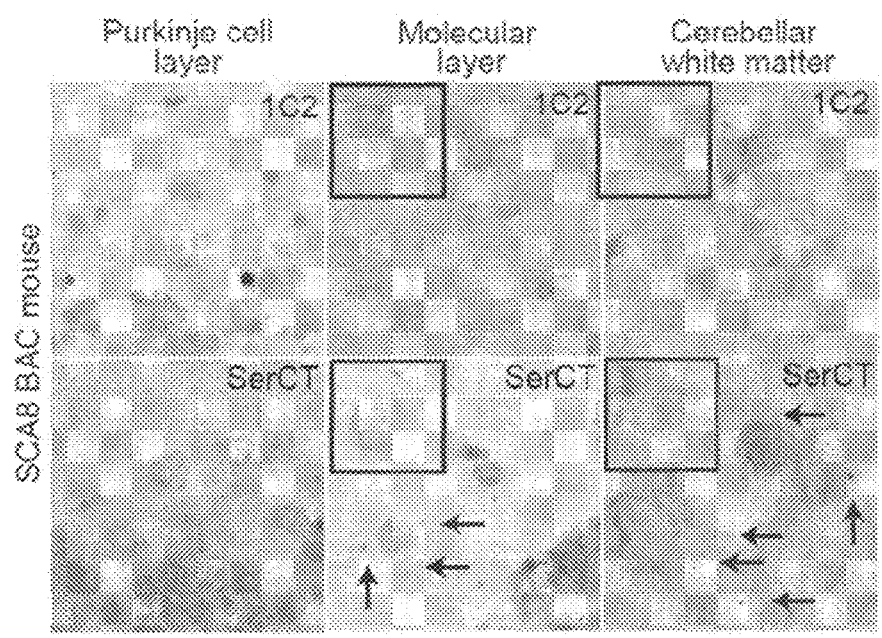

To test if polySer RAN proteins accumulate in SCA8, rabbit polyclonal antibodies directed at two non-overlapping peptide sequences within the unique C-terminal region of the predicted SCA8 polySer protein were generated (FIG. 6A). The specificities of these antibodies were demonstrated using cells transfected with plasmids expressing epitope-tagged polySer protein with the predicted C-terminal region (FIGS. 6B-6D). Immunohistochemistry (IHC) was performed and SCA8 polySer RAN protein was detected in vivo. The IHC distribution of polySer RAN was compared with that of the SCA8 polyGln expansion protein in SCA8 mice. Although both proteins are expressed from ATXN8 sense transcripts, their distribution patterns are strikingly different. IHC performed on serial cerebellar sections show polyGln, but not polySer aggregates accumulate in Purkinje cells. In contrast, polySer but not polyGln aggregates are found in the molecular layer and deep cerebellar white matter (FIG. 6E). PolyGln staining in these regions is primarily nuclear. In contrast, polySer aggregates show perinuclear localization or localization within the neuropil in these regions. Similar to mice. SCA8 polySer and polyGln proteins accumulate in distinct regions in human autopsy tissue, with polySer found primarily in deep cerebellar white matter and polyGln in Purkinje cell nuclei.

In summary, SCA8 polySer and polyGln proteins, which are both expressed from ATXN8 transcripts, show strikingly distinct patterns of accumulation. SCA8 RAN polySer aggregates are primarily found in white matter and neuropil regions throughout the brain. In contrast, polyGln aggregates are found in cerebellar Purkinje cells and other neurons throughout the brain. These data indicate cell specific expression, localization or turnover differences of these proteins lead to their different cellular accumulation patterns, and that polySer RAN proteins may contribute to disease by affecting white matter regions.

SCA8 polySer Aggregates Increase with Age and Disease Progression

Figure 7:
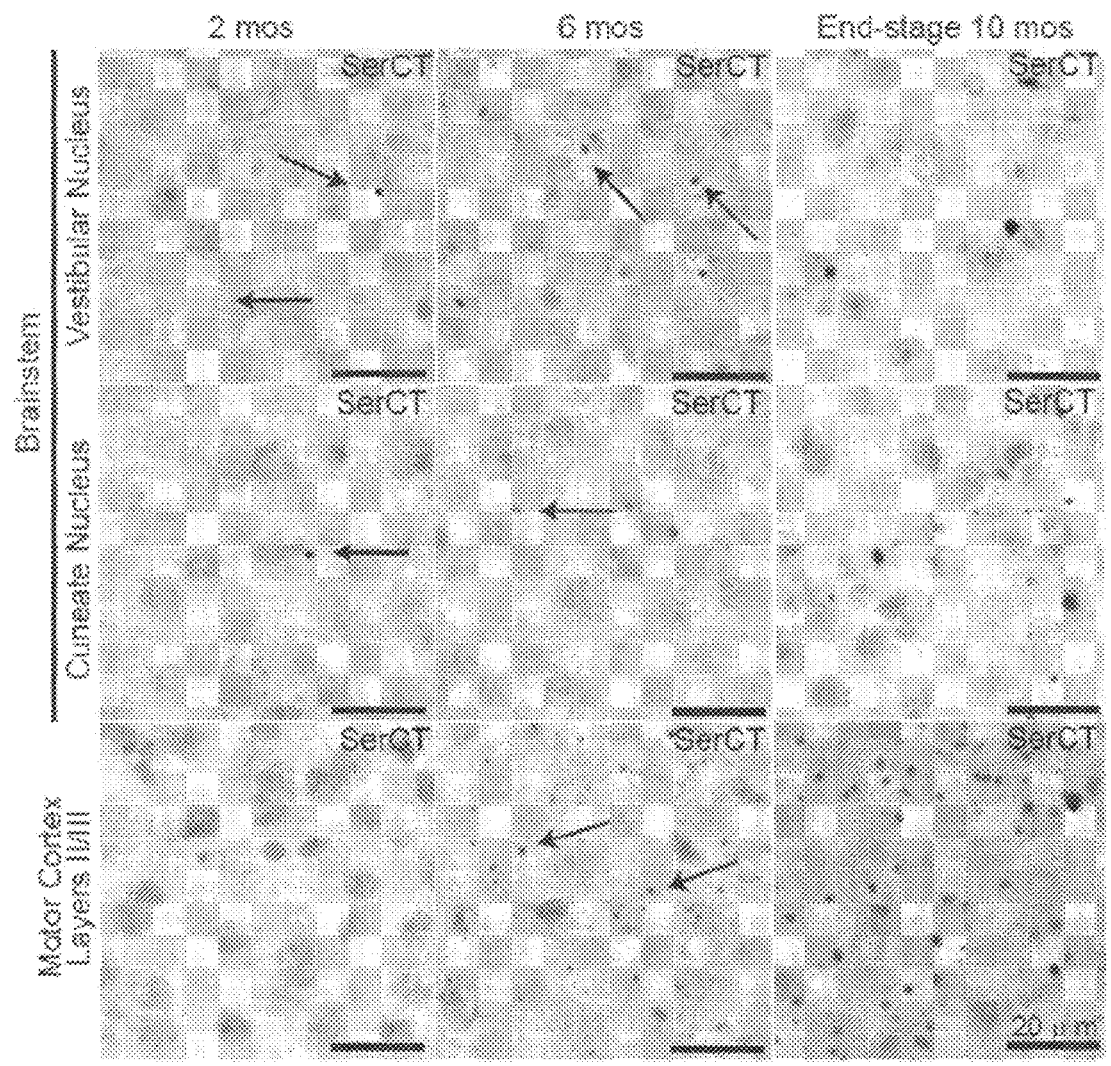
FIG. 7 shows polySer accumulation increases with age and severity of disease. Representative images of the vestibular nucleus, cuncate nucleus, and motor cortex layers II/III of SCA8 BAC mice (n=3) at 2 months (left panels), 6 months (middle panels), and end-stage stained with α-SerCT are shown. Representative aggregates are indicated by arrows.

To address how polySer RAN protein aggregate load changes over time and disease progression IHC at different ages was performed at 2 months 1 when animals show no overt abnormalities), 6 months (when marked phenotypes are apparent and would be fatal without additional care), and at 10 months of age (when animals show advanced end-stage disease). At 2 months of age. IHC revealed very small, pin-like polySer aggregates which were found infrequently in the brainstem (FIG. 7) but were not detectable the frontal cortex. At 6 months of age, the size and the number of polySer RAN aggregates in the brainstem substantially increased and small aggregates were now apparent throughout the frontal cortex. At approximately 10 month of age (end stage with supportive care), polySer aggregates had increased in size and were more abundant in both the brainstem and frontal cortex (FIG. 7).

In summary, polySer RAN protein load increases with age and disease progression in SCA8 mice. Early polySer RAN protein accumulation within the neuropil of the brainstem is consistent with the early motor abnormalities seen in 2 month animals. Additionally, the detection of polySer RAN aggregates throughout the frontal cortex at later stages of the disease is consistent with multiple reports of cortical involvement in SCA8 patients.

RAN polySer Positive White Matter Regions Show Degenerative Phenotypes

Figure 8A:
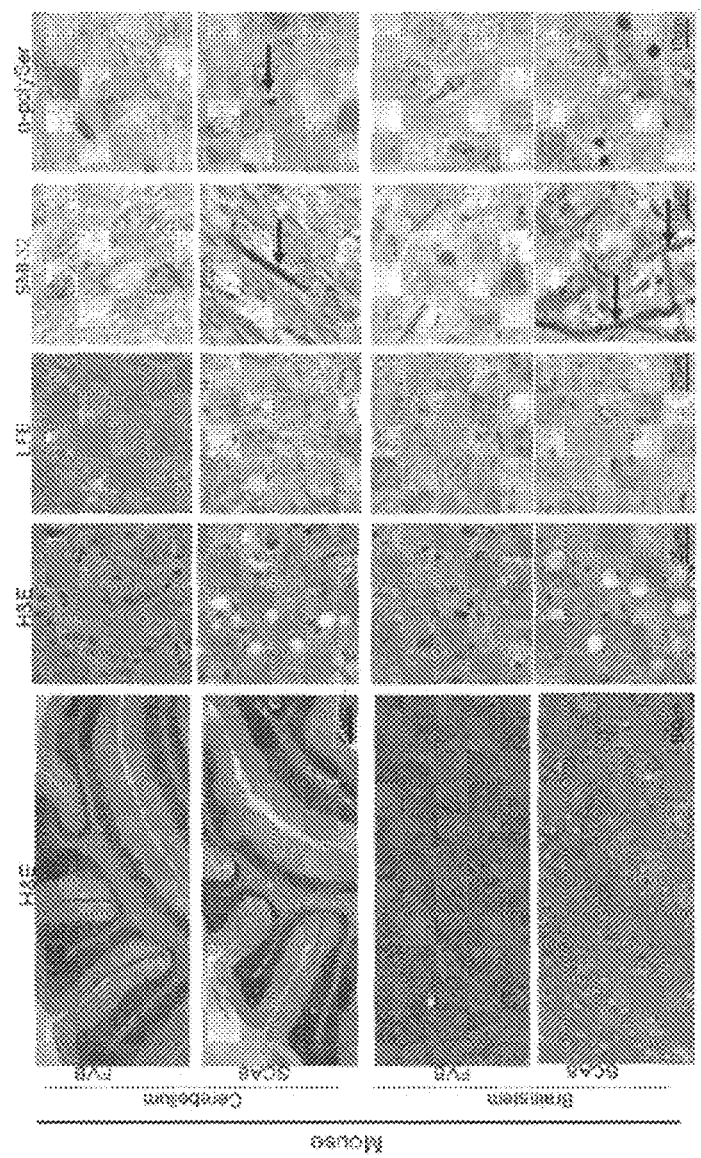
FIGS. 8A-8D show SCA8 BAC mice show white matter abnormalities at sites of polySer accumulation.
Figure 8B:
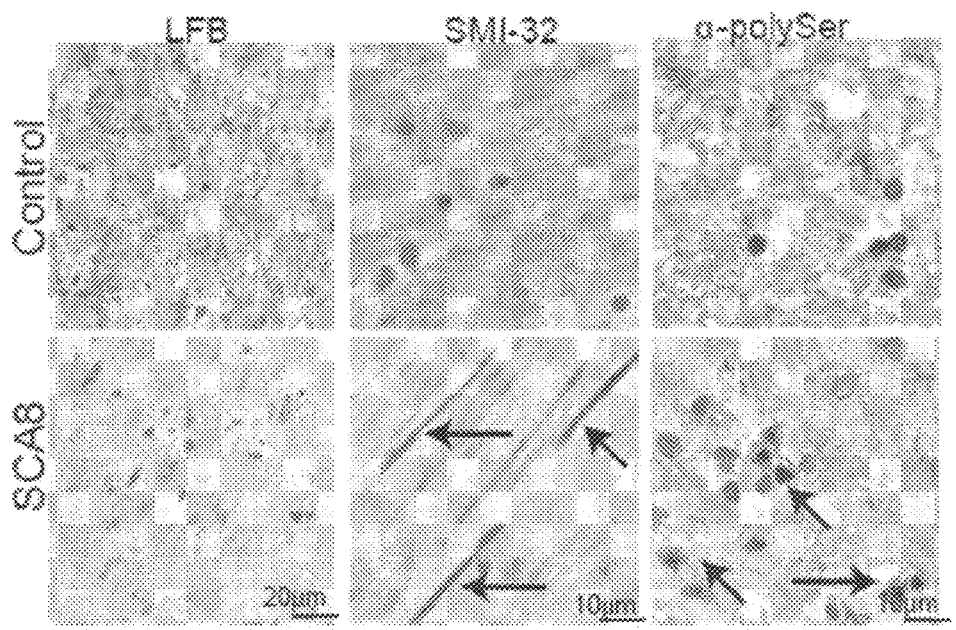

H&E staining of severely affected SCA8 mice indicates widespread vacuolization of subcortical and deep white matter in the cerebellum including the dentate nucleus (FIG. 8A). Vacuolization was also observed in subcortical white matter regions of the cerebral cortex and in white matter tracts throughout the brainstem (FIG. 8A). Serial sections of the cerebellum and brainstem were examined to observe if demyelination and axonal degeneration are found in polySer positive regions. Luxol fast blue (LFB) staining shows demyelination in both the cerebellum and brainstem from SCA8 mice compared to controls. Consistently, IHC using an antibody against the dephosphorylated form of neurofilament H showed evidence of axonal degeneration (FIG. 8A). Similar changes were observed in human autopsy tissue with demyelination and axonal degeneration observed at sites with polySer accumulation (FIG. 8B).

Figure 8C:
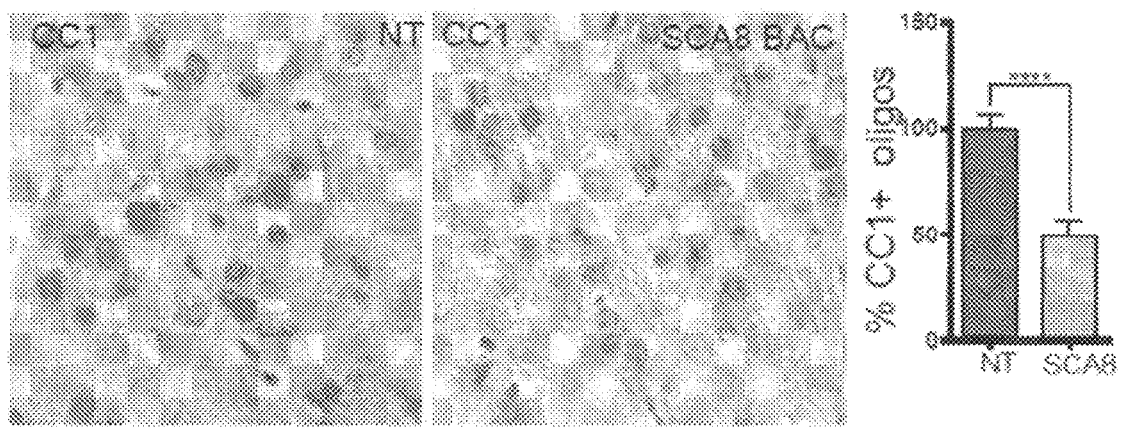
Figure 8D:
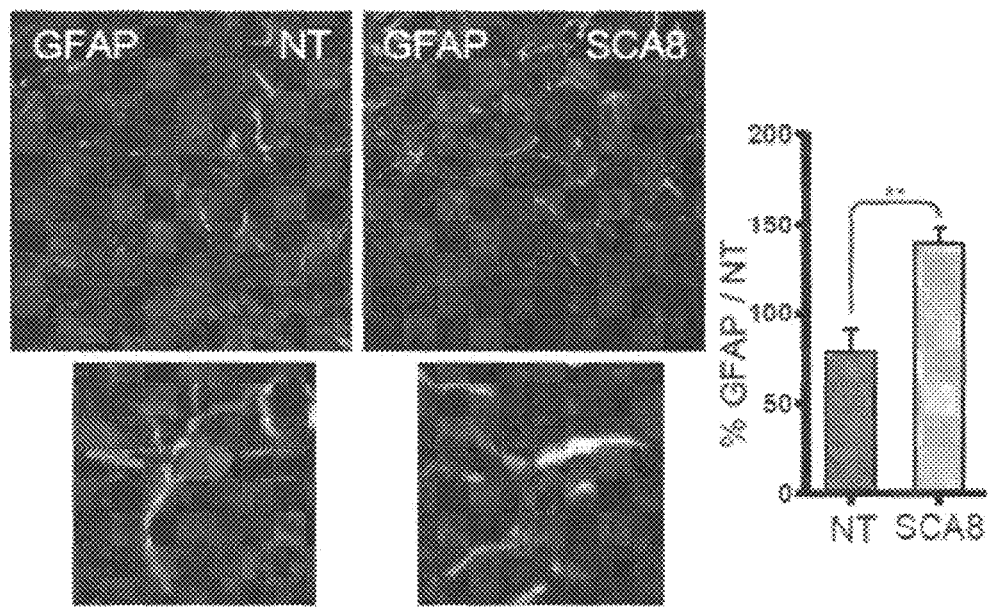

To further characterize the oligodendrocyte abnormalities in the polySer positive white matter regions, IHC using a cytoplasmic marker of mature oligodendrocytes (CC1) was performed in mice. Consistent with the demyelination data, these data show a decreased number of mature oligodendrocytes in the deep cerebellar white matter regions of SCA8 animals compared to controls. (FIG. 8C). Additionally, GFAP staining of the deep cerebellar white matter shows evidence for reactive astrogliosis in SCA8 compared to NT animals with a 50% increase in relative GFAP staining (FIG. 8D).

Taken together these data indicate that polySer positive white matter regions in SCA8 mice show oligodendrocyte loss, astrogliosis, demyelination and axonal degeneration.

Figure 9A:
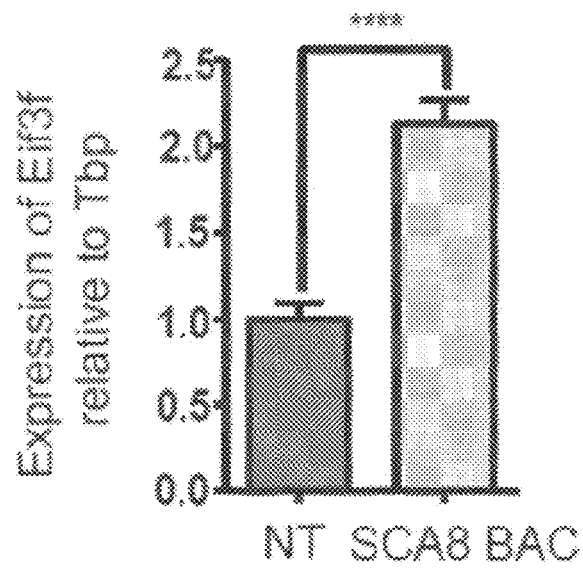
FIGS. 9A-9F show mammalian translation factor eIF3F is upregulated in symptomatic SCA8 BAC mice and can regulate RAN translation.

RAN Translation Modulated by eIF1F, a Translation Factor with Increased White Matter Expression The accumulation of the SCA8 polySer RAN protein in white matter regions indicates that RAN translation may be more efficient in specific cell types or brain regions. Transcriptomic data were analyzed and it was observed that the Eukaryotic translation factor, eIF3F is elevated in white matter. RNAseq data indicated a 2.13 fold increase in eIF3F RNA levels during the late stages of disease correlating with increased RAN protein aggregation compared to control mice (FIG. 9A). These data indicate that eIF3F might increase RAN translation in later stages of the disease and also explain the preferential accumulation of RAN polySer protein in white matter.

Figure 9B:
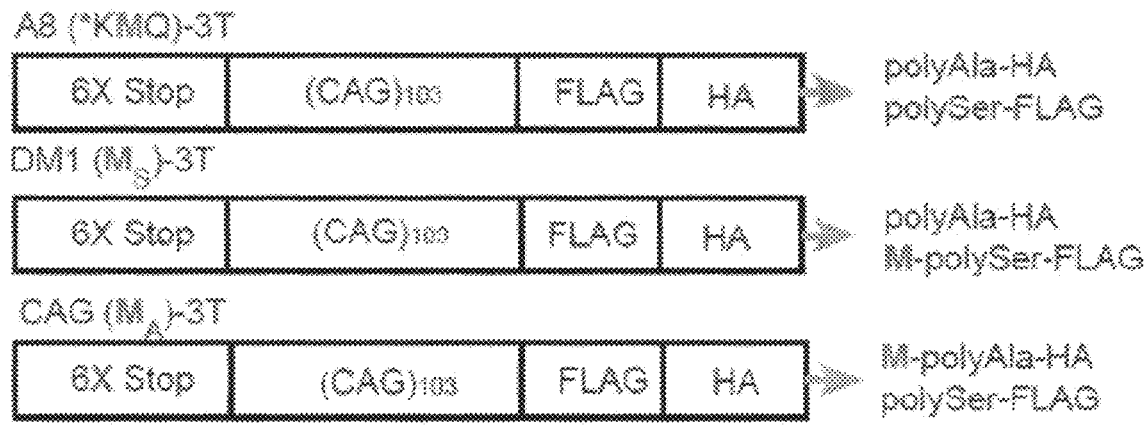
Figure 9C:
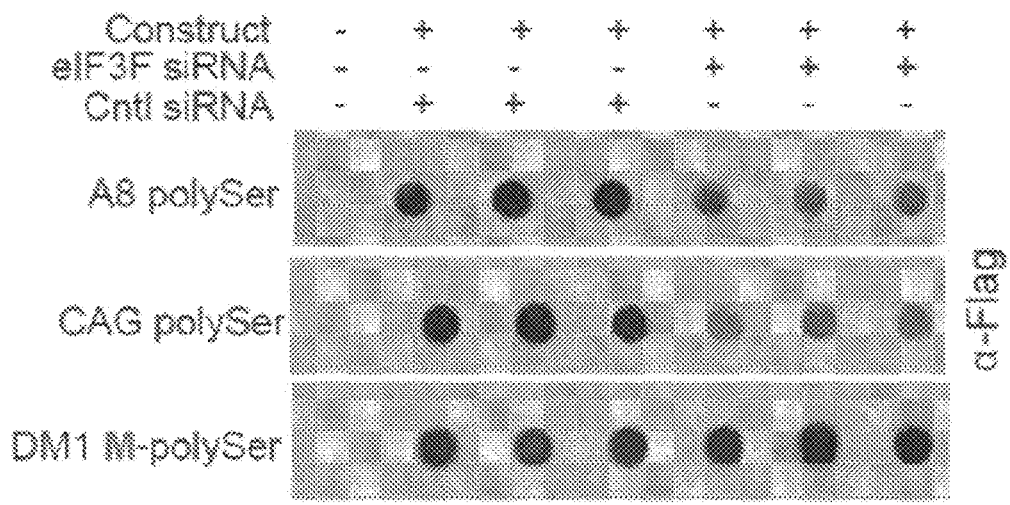
Figure 9D:
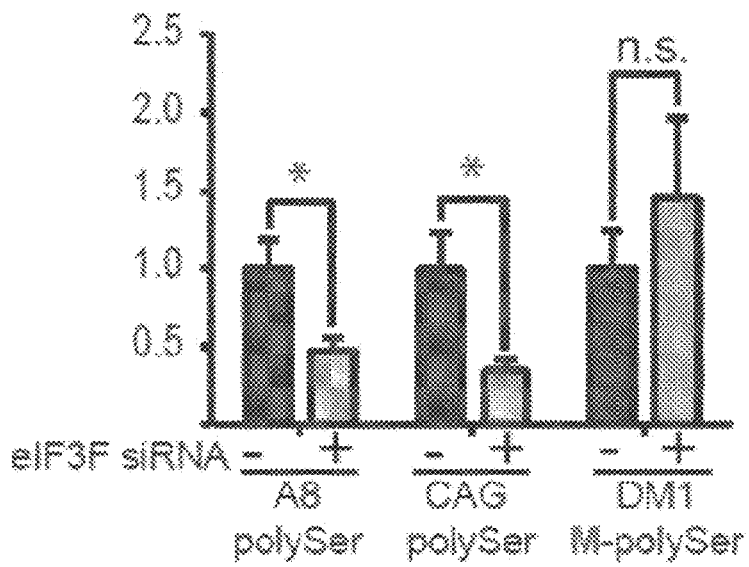
Figure 9E:
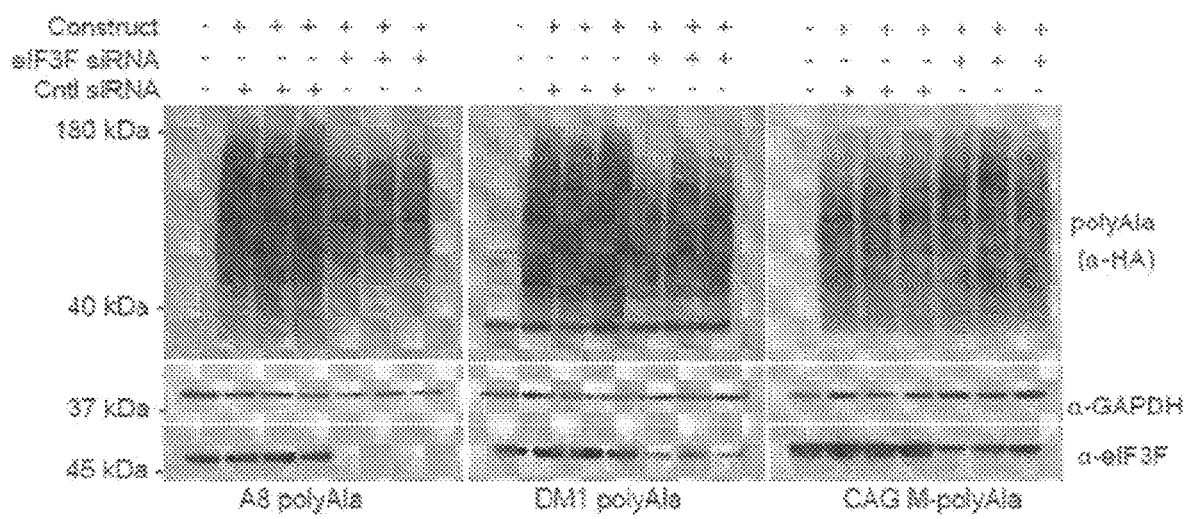
Figure 9F:
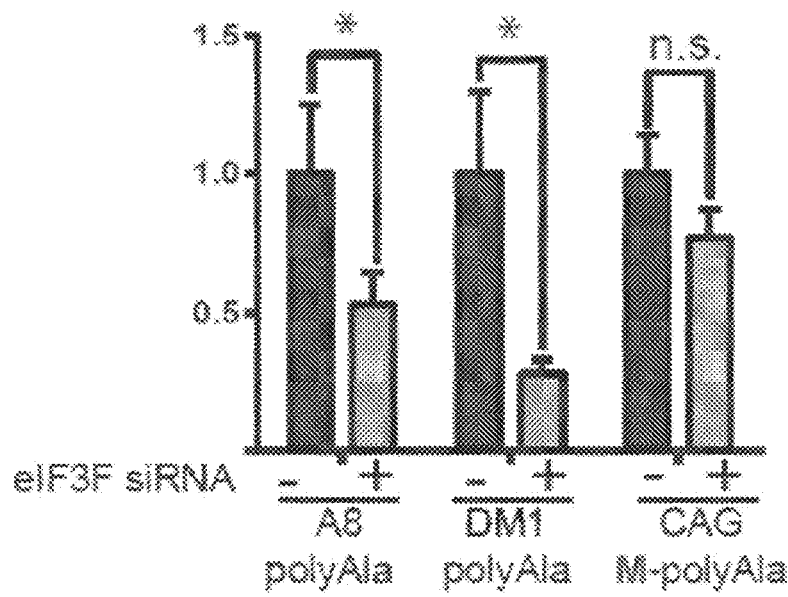

A series of cell culture experiments were performed in which the effects of eIF3F knockdown on expansion proteins expressed from constructs with or without an ATG initiation codon were examined. The effects of eIF3F knockdown on polySer RAN protein expression using minigenes with and without ATG initiation codons in the polySer frame (FIG. 9B) were investigated. siRNA knockdown of eIF3F decreases steady state levels of polySer proteins expressed using the A8 and CAG constructs that do not contain an ATG-initiation codon to 47% ($p<0.05$) and 34% ($p<0.01$) compared to control siRNA (FIG. 9C). In contrast, eIF3F knockdown did not affect polySer levels in cells transfected with the DM1($M_s$)-3T construct, which contains an ATG-initiation codon in the polySer frame (FIG. 9D). Similarly, steady state levels of polyAla RAN proteins expressed from constructs without ATG initiation codon in the polyAla reading frame (A8 and DM1) are decreased by eIF3F knockdown to 53% (p<0.05) and 28% (p<0.05), respectively (FIGS. 9E and 9F). Similar to the polySer results, eIF3F knockdown in the presence of an ATG initiation codon (CAG-3T) did not decrease polyAla accumulation. In summary, these data indicate that RAN translation of polyAla and polySer proteins across expanded CAG repeats uses alternative protein translation machinery that involves eIF3F. In contrast, the presence of an in-frame ATG codon allows recruitment of the canonical preinitiation complex, which is not sensitive to eIF3F levels.

Figure 10A:
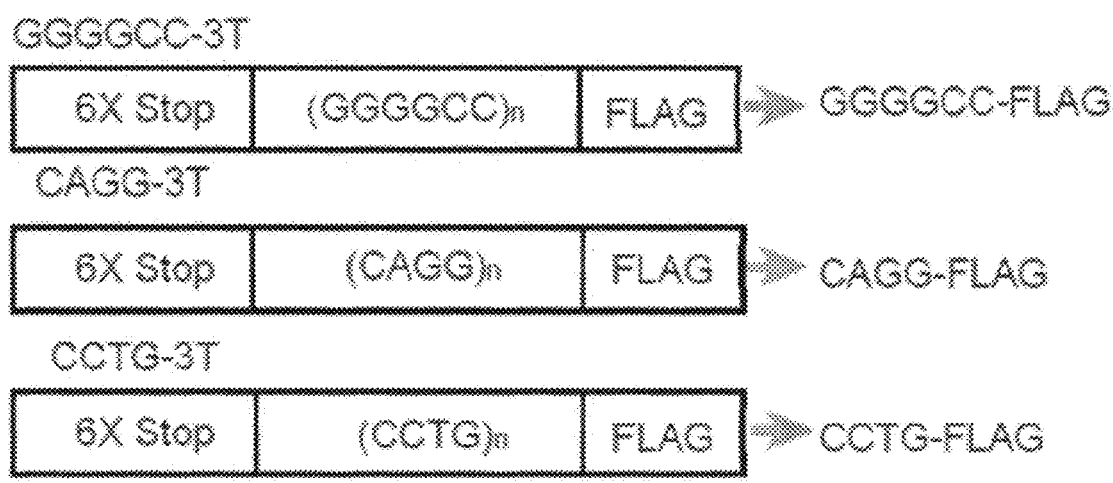
FIGS. 10A-10C show mammalian translation factor eIF3F can regulate across GGGGCC, CAGG and CCTG repeats.
Figure 10B:
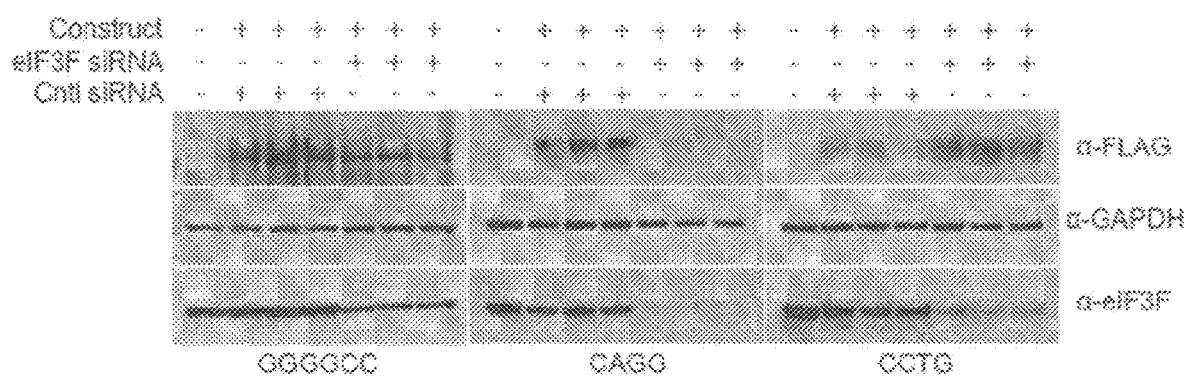
Figure 10C:
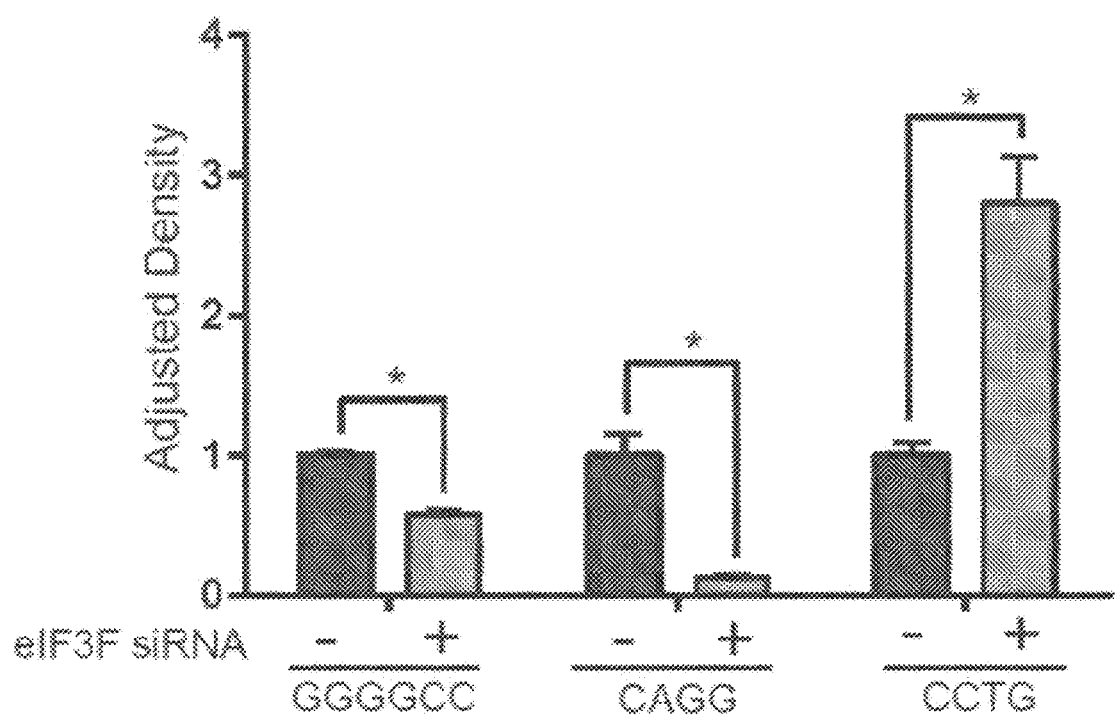

Constructs that express G4C2. CAGG and CCUG expansion RNAs, which are associated with repeat expansion motifs found other diseases (e.g., C9ORF72 ALS/FTD and DM2) were also examined (FIG. 10A). Protein levels of GlyPro (G4C2). GlnAlaGlyArg (SEQ ID NO: 5) (CAGG). LeuProAlaCys (SEQ ID NO: 6) (CCUG) were measured by protein blotting. Similar to the results with the CAG expansion, eIF3F knockdown decreased levels of GP (0.57 p<0.05) and QAGR (0.12 p<0.05) RAN proteins expressed from constructs lacking an ATG initiation codon. In contrast, eIF3F knockdown increased levels of the LPAC tetrapeptide protein expressed across CCUG expansion RNAs (2.8, p<0.05) (FIGS. 10B-10C).

Taken together, these data show RAN translation can be reduced in multiple reading frames and across multiple repeat motifs, including across CAG, G4C2 and CAGG repeats.

Materials and Methods

DNA Constructs and siRNAs

The Flag-polySer-CT construct was generated by subcloning ATNX8 genomic sequence containing a CAG expansion of 82 repeats with 188 bp of downstream sequence into p3XFlag-myc-CMV-24 vector (Sigma, E 6151) in the CAG direction. The genomic DNA used to generate this clone was amplified by PCR using genomic DNA from the SCA8 BAC expansion mice (2878) and using a 5' primer (5'AGCTGAAGCTTGTTAAAAGAAGA-TAATATATTTAAAAAATGCAG 3'; SEQ ID NO: 7) containing an added HindIII restriction enzyme site and the 3' primer (5' AGTCTGAATTCCCTAGTTCTTGGCTCCA-GACTAAC 3'; SEQ ID NO: 8) containing an added EcoRI restriction enzyme site. The 5' primer also contains a T/G base substitution to avoid the insertion of a stop codon in AGC reading frame between N-terminal flag and the repeat tract. The PCR product was cut with HindIII/EcoRI and cloned into p3XFlag-myc-CMV-24 cut with the same enzymes. The presence the N-terminal Flag epitope tag in the polySer (AGC) frame, 82 CAG repeats and 3'flanking region spanning the first stop codon within polySer frame was confirmed by Sanger sequencing. ATG(CAG103)-3T, A8(KMQ)-3T, DM1-Ser(M), GGGGCC-3T were previously generated, siRNA targeting human eIF3F and a control non-targeting siRNA were ordered from a commercial source.

Cell Culture and Transfections

HEK293T cells were cultured in DMEM supplemented with 10% fetal bovine serum (FBS) and incubated at 37° C. in a humid atmosphere containing 5% $CO_2$. Plasmid and siRNA transfections were done with Lipofectamine 2000 (Invitrogen). Cells were collected 48 hours post-transfection for subsequent analysis. For KD experiments, HEK293T cells were transected with 30 nM siRNA using Lipofectamine 2000. 24 h post-transfection, repeat containing plasmid and 30 nM siRNA co-transfected. Cells were collected 48 h after the first second round of transfection.

Production of Rabbit Polyclonal Antibodies

The polyclonal rabbit antibodies against polySer RAN protein were generated by New England Peptide. Rabbit antisera was raised against synthetic peptides Ac-CSSSKARFSNMKD-amide (SEQ ID NO: 9) and Ac-CRVNLSVEAGSQKRQSE-amide (SEQ ID NO: 10) for α-polySer1 and α-polySer2, respectively.

Mouse Samples

SCA8 BAC transgenic lines on the FVB background (Bac exp2, 2878) were used in this example. Hemizygous mice with the SCA8 BAC transgene were confirmed by genotyping PCR. Due to severe motor dysfunction that SCA8 BAC expansion mice exhibits after 5 months of age, additional food (GelDiet, Clear $H_2O$) was provided in the bottom of the cage for animals >5 months. For histological analysis, animals were anesthetized using 100 mg of ketamine and 20 mg of xylazine per kg of body weight and perfused through the ascending aorta with 15 ml of isotonic saline, followed by 10 ml of 10% buffered formalin.

Histology and Immunohistochemistry

For the detection of polySer RAN proteins, brains were collected and frozen in 2-methylbutane cooled with liquid nitrogen. Seven-micrometer sagittal sections were cut using cryostat and fixed in 10% buffered formalin for 15 min. Endogenous peroxidase block was performed in 3% $H_2O_2$ methanol for five minutes. To block nonspecific binding a nonserum block (Biocare Medical. BS966M) was applied for 15 minutes. Primary antisera were applied in 1:10 non-serum block at 4° C. overnight at the following dilutions; α-polySer1 (1:10000), α-polySer2 (1:5000) or corresponding preimmune sera at the same dilutions. The sections were washed three times in 1×PBS and biotin-labeled rabbit secondary antibody (Biolegend, sig-32002) applied at room temperature for 30 min. A horse radish peroxidase conjugated linking reagent (Biolegend, 93028) was applied for 30 min at room temperature and detection was performed by exposure to vector nova red substrate kit (Vector Laboratories, Inc., SK4800). For counterstain, hematoxylin solution (Vector Laboratories, Inc., H3404) was applied for twenty seconds. Slides were dehydrated in graded ethanol and xylene solutions and mounted using Cytoseal 60 (Electron Microscopy Sciences, 18006).

For detection of polySer RAN protein in fixed brain tissue, animals were perfused transcardially with 1×PBS and 10% buffered formalin. Brains were collected and stored in 10% formalin for 24 hours and later removed into 70% ethanol. After histological processing and paraffin embedding, seven-micrometer sagittal sections were cut using a microtome. Sections were deparaffinized in xylene (15 minutes) and rehydrated through an alcohol gradient (10 minutes). Sections were then treated with the following antigen retrieval steps. First, 1 ug/mL proteinase K treatment in 1 mM $CaCl_2$, 50 mM Tris buffer (pH=7.6) for 30 minutes at 37° C. Second, pressure cooked in 10 mM EDTA (pH=6.5) for 15 minutes using microwave as a heat source. Third, 95% formic acid treatment for five minutes. Endogenous peroxidase was blocked in 3% $H_2O_2$ methanol for ten minutes. To block nonspecific binding a nonserum block (Biocare Medical, BS966M) was applied for 15 minutes. Primary antisera were applied in 1:10 non-serum block at 4° C. overnight with α-polySer1 (1:500)), α-polySer2 (1:10000) or corresponding preimmune sera in the same concentrations. The sections were washed three times in 1×PBS and biotin-labeled rabbit secondary antibody (Biolegend. SIG32002) applied at room temperature for 30 min. A horse radish peroxidase conjugated linking reagent was applied for 30 min at room temperature and detection was performed by exposure to the Vector Red Substrate Kit (Vector Laboratories, Inc., SK4800). Hematoxylin solution was applied for twenty seconds (Vector Laboratories. Inc., H3404).

Immunostaining experiments using CC1 (1:1000, Calbiochem), SMI-32 (1:3000, Covance) and α-Flag (1:1000, Sigma) antibodies were performed in similar way as above except that a milder heat induced antigen retrieval was performed in 10 mM citrate buffer (pH=6.0) using a steamer instead of pressure cooker. For hematoxylin and eosin staining, seven micron mouse and human brain sections were deparaffinized in xylene and dehydrated through graded ethanol. The slides were then soaked in hematoxylin (modified Harris. Sigma Aldrich) for 1 min and washed in running distilled water for 10 min. Next, the slides were immersed in Eosin Y (Sigma Aldrich, 71311) for 30 see and washed in distilled water for 10 min. The slides were rehydrated and cover slipped before visualization.

For luxol fast blue (LFB) staining, seven micron mouse and human brain sections were deparaffinized in xylene and hydrated to 95% ethyl alcohol. The sections were left in LFB solution (0.1% Luxol fast blue in 95% ethyl alcohol) at 56° C. overnight. The next day, slides were rinsed in 95% ethyl alcohol and distilled water. Subsequently, the slides were differentiated in the lithium carbonate solution and 70% ethyl alcohol (30 seconds, each) and washed in distilled water. The slides were counterstained in the cresyl violet solution (0.1% cresyl violet in distilled water) for 40 seconds, rinsed in distilled water. The slides were rehydrated and cover slipped before visualization. Images were captured with an Olympus BX51 light microscope.

Statistical Analysis

Statistical significance was assessed by unpaired Student's t test. Statistics were performed using the software package Prism 5 (GraphPad Software).

Western Blotting

Cells were lysed with RIPA (150 mM NaCl, 1% sodium deoxycholate, 1% Triton X-100, 50 mM Tris-HCl) (pH=7.5) buffer with proteinase inhibitors (Roche) at 4° C. shaking 30 minutes. Genomic DNA is sheared by 21-gauge needle, the lysates centrifuges at 4° C. at 15000 g for 15 minutes. Supernatant was taken as soluble fraction and quantified by Bradford assay (Biorad). Lysates were run 4%-12% Bis-Tris gel (Biorad) and transferred to Nitrocellulose membrane. Membranes were blotted with the antibodies at 4° C. shaking overnight: Anti-myc (1:2000, Sigma, F9291), anti-Flag-HRP (1:3000. Sigma. A8592), anti-HA (1:2000, Sigma, H6533), anti-GAPDH (1:10000, Millipore, MAB374) α-polySer1 (1:10000) in 1% milk in phosphate buffered saline with Tween 20 (PBST). Membranes were washed in PBST for 5 minutes three times and incubated in secondary antibody solutions conjugated to horseradish peroxidase (1:2500, GE Healthcare, NA931V) for 45 minutes at room temperature. Membranes were washed again in PBST and developed with the application of the substrate for enhanced chemiluminescence (ECL) for 1 minute (PerkinElmer, NEL10400).

Pellets were resuspended in 2% SDS and incubated at 65° C. Resulting SDS soluble fraction was immobilized onto nitrocellulose membranes with Bio-Dot 96-well microfiltration system (Bio-Rad) under vacuum. The membranes were washed with PBST and blotted using the same protocol as Western blotting.

Example 3

Figure 11A:
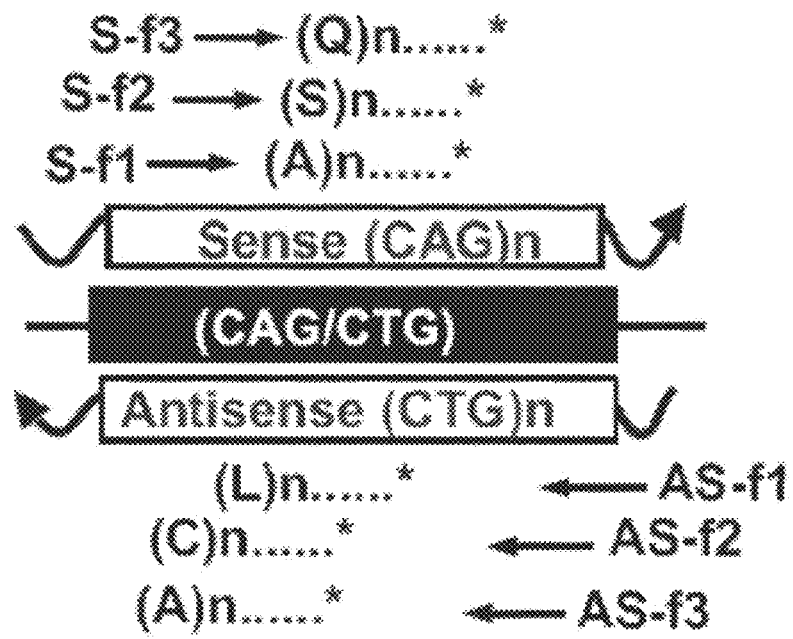
FIGS. 11A-11E show development of an anti-Ser antibody that binds to the poly-Ser repeat.
Figure 11B:
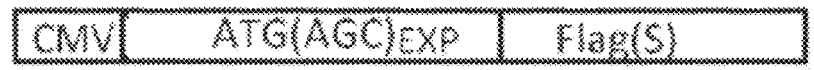
Figure 11C:
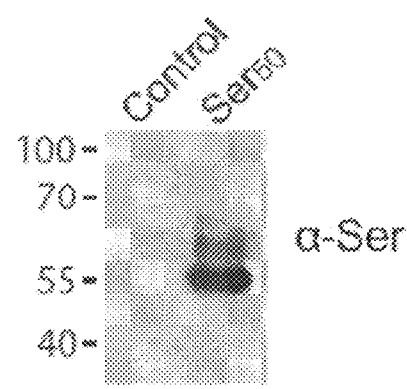

An anti-Ser antibody that binds to poly-serine (polySer) RAN protein was produced (FIGS. 11A-11C). Poly-Ser is produced by translation of the second reading frame of CAG repeats in the sense direction (FIG. 11A). A peptide sequence comprising 10 serine residues (SEQ ID NO:17 was used to produce a polyclonal antibody (anti-Ser) in rabbits. An expression construct encoding a poly-Ser protein having a C-terminal FLAG tag was also produced. Immunoblot analysis indicates specific binding of anti-Ser to poly-Ser protein (FIG. 11C).

Figure 11D:
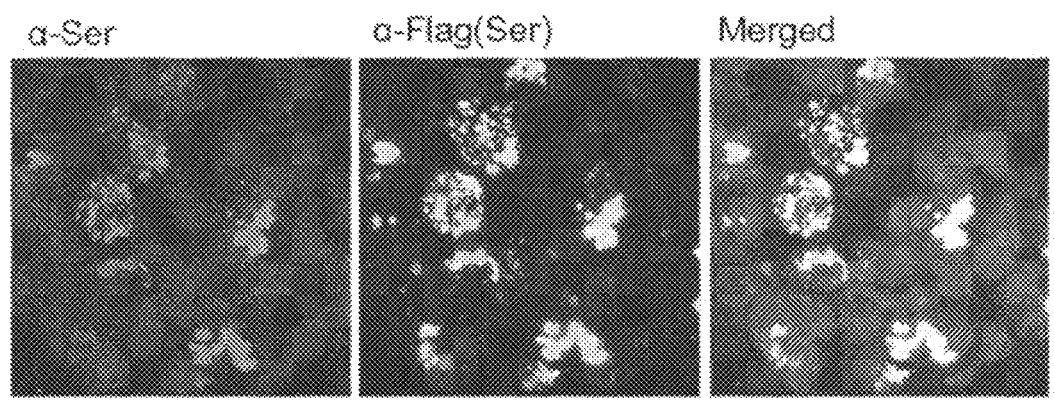
Figure 11E:
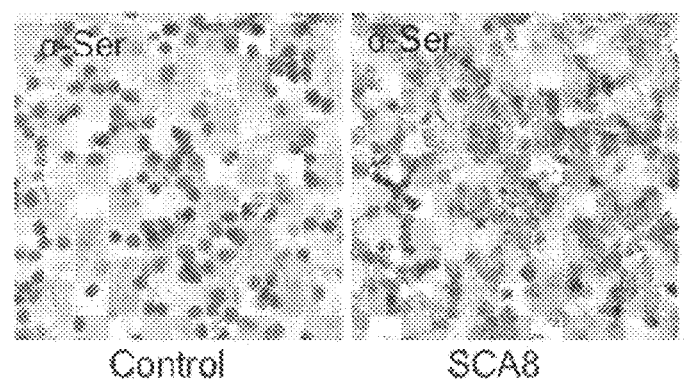

HEK293T cells were transfected with the expression construct encoding polySer and immunofluorescence assays were performed. Data indicate that poly-Ser protein was detected by both anti-FLAG and anti-Ser antibodies (FIG. 11D). Anti-Ser antibody also stained poly-Ser protein in SCA8 human autopsy tissue but not control human autopsy tissue (FIG. 11E).

It was observed that RAN polySer shows a distinct accumulation pattern primarily in white matter regions and co-localize with white matter abnormalities. It was observed that early white matter changes play a pathogenic role in SCA8, indicating that modulation of translation machinery is a viable therapeutic option to decrease RAN translation. The accumulation of polySer RAN proteins in human SCA8 brain also indicates that polySer RAN proteins are a suitable target for immunotherapy.

A number of neurodegenerative diseases are accompanied with an abnormal accumulation of misfolded proteins in insoluble intracellular or extracellular aggregates. In some embodiments, the toxicity of misfolded protein aggregates resides in the insoluble aggregates. In some embodiments, the toxicity of misfolded protein aggregates resides in their soluble oligomers. Thus in some embodiments, anti-RAN protein antibodies (e.g., anti-Ser) target (e.g., immunospecifically bind to) and clear RAN protein aggregates and oligomers in a subject. In some embodiments, an anti-RAN protein antibody binds to an intracellular RAN protein (e.g., binds to a RAN protein in the cytoplasm or nucleus of a cell). In some embodiments. RAN proteins (such as polyGA, poly-GP, poly-PA, etc.) are transmitted between cells. In some embodiments, an anti-RAN protein antibody binds to an extracellular RAN protein (e.g., binds to a RAN protein outside of the extracellular membrane of a cell).

In some embodiments, an anti-RAN protein antibody mediates antibody-induced phagocytosis of pathological protein deposits, direct antibody-mediated disruption of aggregates, neutralization of toxic soluble proteins, neutralization of aggregated proteins, or blocking cell-to-cell transmission of misfolded proteins.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including." "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures. Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of modulating repeat-associated non-ATG protein (RAN protein) translation, the method comprising contacting a cell expressing a RAN protein with an effective amount of a selective modulator of eukaryotic initiation factor 3 subunit f (eIF3f),
wherein the selective modulator of eIF3f is a protein, a small molecule, or an inhibitory nucleic acid selected from the group consisting of dsRNA, siRNA, shRNA, miRNA, artificial miRNA (amiRNA), and an antisense oligonucleotide (ASO).

2. The method of claim 1, wherein the selective modulator of eIF3f directly or indirectly inhibits a gene encoding eIF3f (eIF3F) and/or reduces expression of eIF3f.

3. The method of claim 1, further comprising contacting the cell with a selective modulator of eukaryotic initiation factor 3 subunit m (eIF3m).

4. The method of claim 3, wherein the selective modulator of eIF3m directly or indirectly inhibits a gene encoding eIF3m (eIF3M) and/or reduces expression of eIF3m.

5. The method of claim 1, wherein the cell is located in a subject, optionally wherein the cell is located in the brain of the subject.

6. The method of claim 1, wherein the RAN protein is a poly-Alanine, poly-Leucine, poly-Serine, poly-Cysteine, poly-Glutamine, poly-Leu-Pro-Ala-Cys (SEQ ID NO: 6), poly-Gln-Ala-Gly-Arg (SEQ ID NO: 5), poly-Gly-Pro, poly-Gly-Arg, poly-Gly-Ala, poly-Pro-Ala, or poly-Pro-Arg.

7. The method of claim 1, wherein the RAN protein is not poly-Glutamine.

8. The method of claim 1, wherein the RAN protein is encoded by a gene associated with Huntington's disease (HD, HDL2), Fragile X Tremor Ataxia Syndrome (FXTAS), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2), Spinocerebellar Ataxia 3 (SCA3), Spinocerebellar Ataxia 6 (SCA6), Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuchs' Corneal Dystrophy (CTG181).

9. The method of claim 1, wherein the RAN protein is a poly-Alanine, poly-Leucine, poly-Serine, poly-Cysteine, or poly-Glutamine.

10. The method of claim 1, wherein the RAN protein is encoded by a gene comprising CAG, CAGG, GGGGCC, or CCTG expansion repeats.

11. The method of claim 1, wherein the selective modulator of eIF3f is an siRNA.

12. The method of claim 1, wherein the selective modulator of eIF3f is an shRNA.

13. The method of claim 3, wherein the selective modulator of eIF3m is an inhibitory nucleic acid selected from the group consisting of dsRNA, siRNA, shRNA, miRNA, artificial miRNA (amiRNA), and an antisense oligonucleotide (ASO).

14. The method of claim 13, wherein the selective modulator of eIF3m is an siRNA or an shRNA.

15. The method of claim 1, wherein the method further comprises contacting the cell with an additional therapeutic agent for a disease associated with RAN protein translation.

16. The method of claim 15, wherein the additional therapeutic agent is an antibody.

17. The method of claim 16, wherein the antibody binds specifically to a RAN repeat expansion.

18. The method of claim 16, wherein the antibody binds specifically to a unique region of a RAN protein that is C-terminal to the repeat expansion.

19. The method of claim 5, wherein the subject has a disease associated with RAN protein translation.

20. The method of claim 19, wherein the disease is Huntington's disease (HD, HDL2), Fragile X Tremor Ataxia Syndrome (FXTAS), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2), Spinocerebellar Ataxia 3 (SCA3), Spinocerebellar Ataxia 6 (SCA6), Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuchs' Corneal Dystrophy (CTG181).

* * * * *